US012762817B2

(12) United States Patent
Luisi et al.

(10) Patent No.: US 12,762,817 B2
(45) Date of Patent: Oct. 13, 2026

(54) CUSTOM MANUFACTURED PARTITIONED CRANIAL REMODELING ORTHOSIS DEVICE

(71) Applicant: CRANIAL TECHNOLOGIES, INC., Tempe, AZ (US)

(72) Inventors: Jerold N Luisi, Phoenix, AZ (US); George E Kechter, Loves Park, IL (US); Timothy R Littlefield, Mesa, AZ (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 122 days.

(21) Appl. No.: 18/900,794

(22) Filed: Sep. 29, 2024

(65) Prior Publication Data

US 2025/0022243 A1 Jan. 16, 2025

Related U.S. Application Data

(63) Continuation-in-part of application No. 17/180,180, filed on Feb. 19, 2021, now Pat. No. 12,633,070, and (Continued)

(51) Int. Cl.
*G06T 19/20* (2011.01)
*A61F 5/058* (2006.01)
(Continued)

(52) U.S. Cl.
CPC .......... *G06T 19/20* (2013.01); *A61F 5/05891* (2013.01); *B29C 64/386* (2017.08); (Continued)

(58) Field of Classification Search
CPC ........... A42C 2/007; A42B 3/32; A42B 3/124; A42B 3/128; A42B 3/063; A42B 3/00; (Continued)

(56) References Cited

U.S. PATENT DOCUMENTS 5,094,229 A * 3/1992 Pomatto ............. A61F 5/05883 602/17
5,531,520 A 7/1996 Grimson
(Continued)

FOREIGN PATENT DOCUMENTS

EP 3231307 A1 * 10/2017 ............... A42B 3/32
EP 4327788 A1 * 2/2024 ......... A61F 5/05891
(Continued)

OTHER PUBLICATIONS

Latruffe, Sports Helmet, Oct. 18, 2017.*
(Continued)

*Primary Examiner* — Kari K Rodriquez
*Assistant Examiner* — Andrew Jun-Wai Mok
(74) *Attorney, Agent, or Firm* — Donald J Lenkszus

(57) ABSTRACT

A custom manufactured cranial remodeling orthosis device for modifying the shape of a subject's head is described. The cranial remodeling orthosis device comprises a plurality of device pieces manufactured with additive manufacture material. Each of the device pieces comprising one or more integral connecting portions. The plurality of device pieces are interconnected together utilizing the one or more integral connecting portions.

14 Claims, 15 Drawing Sheets

Related U.S. Application Data a continuation of application No. 16/925,700, filed on Jul. 10, 2020, now Pat. No. 11,776,228, and a continuation of application No. 15/474,684, filed on Mar. 30, 2017, now Pat. No. 10,710,356.

(51) Int. Cl.

| | |
|---|---|
| ***B29C 64/386*** | (2017.01) |
| ***B29K 105/04*** | (2006.01) |
| ***B29L 31/48*** | (2006.01) |
| ***B33Y 30/00*** | (2015.01) |
| ***B33Y 50/00*** | (2015.01) |
| ***B33Y 50/02*** | (2015.01) |
| ***B33Y 80/00*** | (2015.01) |

(52) U.S. Cl.

CPC ............... *B33Y 30/00* (2014.12); *B33Y 50/00* (2014.12); *B33Y 50/02* (2014.12); *B33Y 80/00* (2014.12); *B29K 2105/04* (2013.01); *B29L 2031/4807* (2013.01); *G06T 2210/22* (2013.01); *G06T 2210/41* (2013.01); *G06T 2219/2016* (2013.01)

(58) Field of Classification Search

CPC ......... A42B 3/003; A42B 1/201; A42B 1/205; A42B 1/206; A42B 1/22; A61B 5/6814; B29L 2031/4807; B33Y 80/00; A61F 13/12; A61F 5/01; A61F 5/3707; A61F 5/05883; A61F 5/05891

See application file for complete search history.

(56) References Cited

U.S. PATENT DOCUMENTS

| | | | | |
|---|---|---|---|---|
| 5,666,670 | A | 9/1997 | Ryan | |
| 5,999,840 | A | 12/1999 | Grimson | |
| 6,340,353 | B1 | 1/2002 | Pomatto | |
| 6,423,019 | B1 | 7/2002 | Papay | |
| 6,428,494 | B1 | 8/2002 | Schwenn | |
| 6,592,536 | B1 | 7/2003 | Argenta | |
| 7,566,313 | B1 | 7/2009 | Argenta | |
| 10,016,941 | B1 | 7/2018 | Beard | |
| 10,463,525 | B2 | 11/2019 | Littlefield | |
| 10,695,211 | B2 | 6/2020 | Mottram | |
| 10,726,617 | B2 | 7/2020 | Littlefield | |
| 11,331,205 | B2 | 5/2022 | Parr | |
| 2002/0010408 | A1 | 1/2002 | Pomatto | |
| 2003/0195450 | A1 | 10/2003 | Argenta | |
| 2004/0015118 | A1 | 1/2004 | Sklar | |
| 2004/0179728 | A1 | 9/2004 | Littlefield | |
| 2004/0197016 | A1 | 10/2004 | Littlefield | |
| 2004/0228519 | A1 | 11/2004 | Littlefield | |
| 2004/0230149 | A1 | 11/2004 | Littlefield | |
| 2004/0230545 | A1 | 11/2004 | Littlefield | |
| 2004/0236708 | A1 | 11/2004 | Littlefield | |
| 2006/0010559 | A1 | 1/2006 | Hamlet | |
| 2006/0101559 | A1 | 5/2006 | Moore | |
| 2009/0118654 | A1 | 5/2009 | Qu | |
| 2009/0316965 | A1 | 12/2009 | Mailling | |
| 2010/0238273 | A1 | 9/2010 | Luisi | |
| 2010/0239135 | A1 | 9/2010 | Luisi | |
| 2010/0292963 | A1 | 11/2010 | Schroeder | |
| 2011/0132379 | A1 | 6/2011 | Lee | |
| 2012/0110828 | A1 | 5/2012 | Luisi | |
| 2012/0113116 | A1 | 5/2012 | Luisi | |
| 2012/0114201 | A1 | 5/2012 | Luisi | |
| 2012/0114223 | A1 | 5/2012 | Luisi | |
| 2012/0163901 | A1 | 6/2012 | Luisi | |
| 2012/0195994 | A1 | 8/2012 | El-Siblani | |
| 2012/0296249 | A1 | 11/2012 | Gordon | |
| 2013/0033482 | A1 | 2/2013 | Luisi | |
| 2013/0289459 | A1 | 10/2013 | Bernardoni | |
| 2014/0201889 | A1 | 7/2014 | Pietrzak | |
| 2014/0256209 | A1 | 9/2014 | Norman | |
| 2014/0274456 | A1 | 9/2014 | Cardani | |
| 2014/0371897 | A1 | 12/2014 | Lin | |
| 2015/0057784 | A1 | 2/2015 | Butler | |
| 2015/0100007 | A1 | 4/2015 | Gilmer | |
| 2015/0210007 | A1 | 7/2015 | Durand | |
| 2015/0223900 | A1 | 8/2015 | Wiebe | |
| 2015/0230959 | A1 | 8/2015 | Gilmer | |
| 2015/0313305 | A1 | 11/2015 | Daetwyler | |
| 2016/0015552 | A1* | 1/2016 | Ono | A61F 5/3707 602/17 |
| 2016/0038332 | A1 | 2/2016 | Gilmer | |
| 2016/0151976 | A1 | 6/2016 | Littlefield | |
| 2016/0184100 | A1 | 6/2016 | Joganic | |
| 2016/0185046 | A1 | 6/2016 | Littlefield | |
| 2016/0191900 | A1 | 6/2016 | Littlefield | |
| 2016/0287425 | A1 | 10/2016 | Gilmer | |
| 2016/0349738 | A1 | 12/2016 | Sisk | |
| 2018/0280186 | A1 | 10/2018 | Littlefield | |
| 2018/0280187 | A1 | 10/2018 | Littlefield | |
| 2018/0280188 | A1 | 10/2018 | Littlefield | |
| 2018/0281312 | A1 | 10/2018 | Littlefield | |
| 2018/0281313 | A1 | 10/2018 | Littlefield | |
| 2018/0281314 | A1 | 10/2018 | Littlefield | |
| 2018/0281315 | A1 | 10/2018 | Littlefield | |
| 2018/0344505 | A1 | 12/2018 | Gilmer | |
| 2019/0015238 | A1* | 1/2019 | Mottram | A61F 5/05891 |
| 2021/0205099 | A1 | 7/2021 | Parr | |
| 2022/0226130 | A1 | 7/2022 | Parr | |
| 2022/0370225 | A1 | 11/2022 | Broze | |

FOREIGN PATENT DOCUMENTS

| | | | |
|---|---|---|---|
| JP | 2022017025 | | 1/2022 |
| JP | 2022017025 | A * | 1/2022 |
| PL | 220385 | B1 | 10/2012 |
| PL | 408607 | A1 | 10/2014 |
| WO | WO/2014/081078 | | 5/2014 |
| WO | WO2018195602 | | 1/2018 |

OTHER PUBLICATIONS

Ono, Cranial Shape Correction Helmet, Jan. 25, 2022.*

3D Printing Aids Babies Healing from Flat Head Syndrom, https://3dprint.com/84519/3d-print-helmets-flat-head/, 3D Printing, Published Jul. 27, 2015.

Osteo3d Makes a Difference with 3D Printed Helmet for 5-Month-Old craniosynostosis Patient, https://3dprint.com/97581/osteo3d-3d-printed-helmet/, Published Sep. 25, 2015.

https://3dprintingindustry.com/news/now-can-3d-print-memory-foam-34265/, Now You Can 3D Print With Memory Foam, Oct. 8, 2014.

https://govinfo.gov/content/pkg/FR-2015-05-21/pdf/2015-11756.pdf, 49 CFR Part 571, pp. 29458-29486; DOT.

https://www.shapeways.com/blog/archives/408-3d-printing-virus-for-sti-file-type.html, Apr. 1, 2010.

Profis, Sharon, DIY:3D printing custom iPhone case, Jul. 31, 2012, retrieved on Aug. 8, 2019,; DIY3D (Year: 2012).

https://www.mcortechnologies.com/trends-3d-scan-print-applications-blog_trashed/; Mar. 23, 2015; Retrieved Sep. 17, 2019 (Year: 2015).

Maundy, How to create your own 3D printed iPhone case, Published Apr. 5, 2012, Retrieved on Jan. 25, 2020 (Year: 2012).

* cited by examiner

CUSTOM MANUFACTURED PARTITIONED CRANIAL REMODELING ORTHOSIS DEVICE

This application is a continuation-in-part of U.S. patent application Ser. No. 17/180,180 filed Feb. 19, 2021, which is a continuation of U.S. patent application Ser. No. 16/925,700 filed Jul. 10, 2020, now U.S. Pat. No. 11,776,228, which is a continuation of Ser. No. 15/474,684 filed Mar. 30, 2017, now U.S. Pat. No. 10,710,356. The parent application is related to U.S. Pat. Nos. 10,846,925; 10,703,084; 10,726,617; 10,463,525; 10,561,521; 10,603,203; and 10,682,846. All the aforesaid Applications and Patents being assigned to and owned by the Applicant of this invention. The disclosures of all the above patents are incorporated in their entireties herein by reference.

The present invention pertains to custom cranial remodeling orthosis devices and methods of manufacturing such devices utilizing additive manufacturing.

The applicant of the present invention has pioneered the treatment of plagiocephaly in infants through the use of custom cranial remodeling orthosis devices that are each custom manufactured for each infant patient. The applicant has also pioneered the customized manufacture of such devices.

Methods of manufacturing custom cranial remodeling devices comprise capturing a three-dimensional digital image of the entirety of a patient's head to produce a digital data file that represents a three-dimensional digital image of the entirety of a desired head shape for the patient. The digital data file is processed to produce a cranial remodeling orthosis device data file that may be utilized by additive manufacturing apparatus such as a 3D printer.

Although it is advantageous to utilize additive manufacture for cranial remodeling orthosis devices, current additive manufacture methods of manufacturing custom cranial remodeling orthosis devices manufacture only whole custom cranial remodeling orthosis device in an additive manufacture production or build chamber at a time. The time to manufacture a single whole custom cranial remodeling orthosis device is typically excessively long.

When it is necessary to treat large numbers of patients, it is desirable to provide cranial remodeling orthosis devices and methods of manufacturing such devices that increases the manufacturing throughput of cranial remodeling orthosis devices and uses additive manufacture more efficiently and cost effectively.

SUMMARY

In one illustrative embodiment of a method of manufacturing, cranial remodeling orthosis device data files for a plurality of custom cranial remodeling orthosis devices are combined into a nested array of device data files and the nested array of device files is provided to an additive manufacture apparatus. The additive manufacture apparatus concurrently manufactures the plurality of cranial remodeling orthosis devices in the production or build chamber of the additive manufacture apparatus.

In one illustrative embodiment of a custom cranial remodeling orthosis device, the cranial remodeling orthosis device comprises a plurality of device portions that are assembled together into an integrated cranial remodeling orthosis device.

Each cranial remodeling orthosis device portion comprises one or more integrally formed connection portions. Each adjacent cranial remodeling orthosis device portion includes corresponding integrally formed connection portions. The cranial remodeling orthosis device is assembled by affixing each cranial remodeling orthosis device portion to one or more adjacent portion utilizing the integrally formed connection portions and corresponding connection portions.

In one illustrative embodiment of a method of additive manufacturing, each cranial remodeling orthosis device data file is partitioned to form a plurality of cranial remodeling orthosis device portion data files. The device portion data files for a plurality of cranial remodeling orthosis devices are arranged into a nested array data file. The nested array data file is then additively manufactured to concurrently manufacture the device portions for the plurality of cranial remodeling orthosis devices in a build chamber. The resulting cranial remodeling orthosis device portions are assembled into the plurality of cranial remodeling orthosis devices.

Various illustrative embodiments of a cranial remodeling orthosis device comprise a plurality of portions that are assembled together to form a unitary cranial remodeling orthosis device. The plurality of device portions is manufactured by partitioning a cranial remodeling orthosis device data file and adding integrally formed connection portions in the cranial remodeling orthosis device portions. The connection portions are utilized to affix each device portion to one or more adjacent portions.

In various illustrative embodiments, a plurality of cranial remodeling device portion data files is combined into a nested array device portion data file. The nested array device portion data file is utilized by additive manufacture apparatus to concurrently manufacture a plurality of corresponding cranial remodeling orthosis device portions that, after manufacture, are assembled into cranial remodeling orthosis devices.

BRIEF DESCRIPTION OF THE DRAWING

The invention will be better understood by a reading of the following detailed description of embodiments of the invention in conjunction with the drawing figures in which like reference indicators designate like elements and in which.

DETAILED DESCRIPTION

Figure 1:
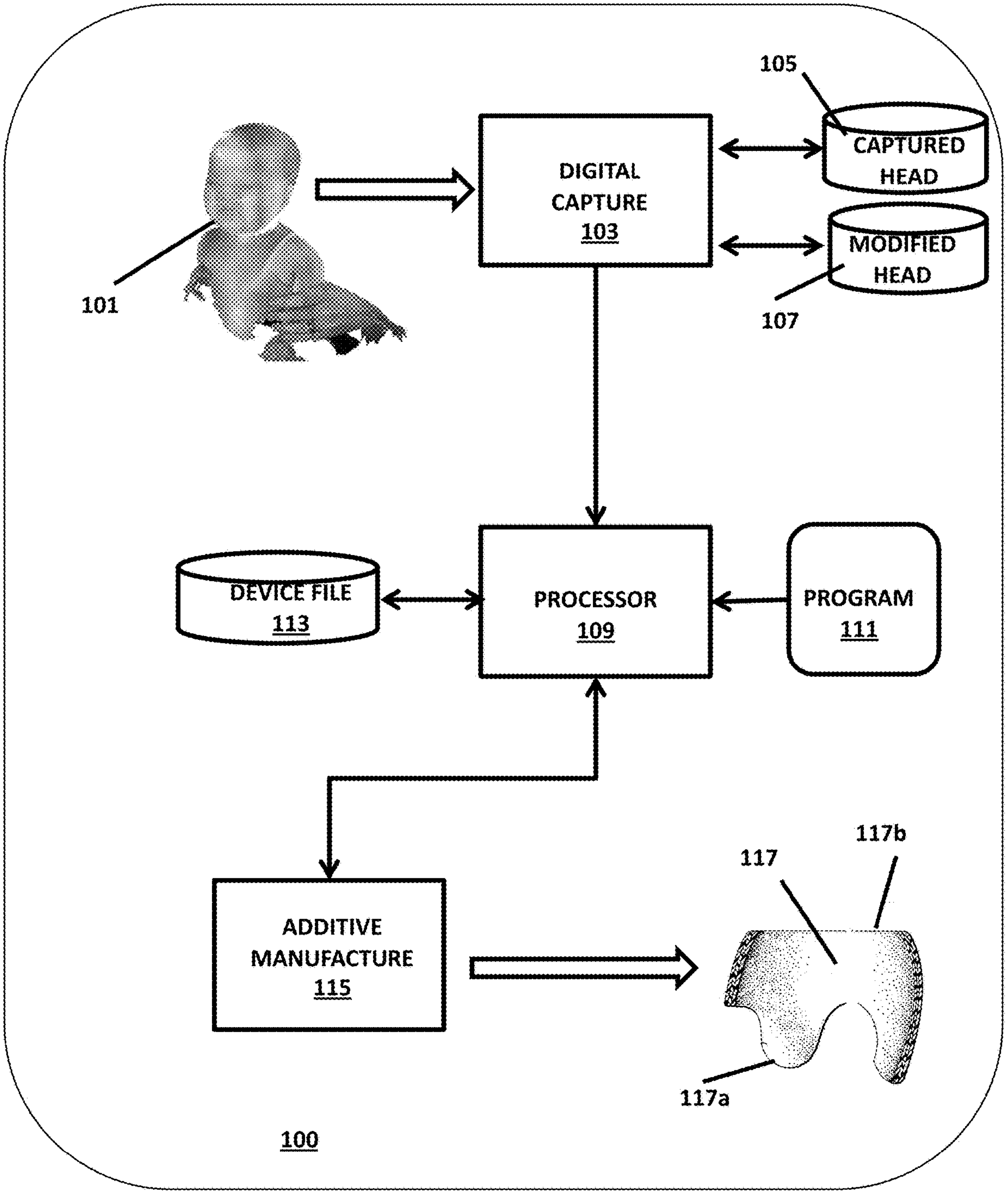
FIG. 1 illustrates an embodiment of a point of service manufacture facility.

In the following description, additive manufacturing apparatus is utilized to manufacture the various embodiments of cranial remodeling orthotic devices. Additive manufacture apparatuses are commonly known as 3D printers.

There are a variety of 3D printers that are commercially available utilizing a variety of methodologies.

Additive manufacture methodologies have been classified into seven categories. The seven categories of printers are material extrusion, sheet lamination, binder jetting, material jetting, directed energy jetting, vat photopolymerization, and fusion bed. There are variations of the different categories. In addition, each category may be implemented using more than one related methodology.

Of particular interest in the manufacture of cranial remodeling orthotic devices is fusion bed additive manufacture. Fusion bed additive manufacture may be of at least four different types, i.e., Direct metal laser sintering (DMLS), selective laser sintering (SLS), and selective laser melting (SLM) use laser fusion, electron beam melting (EBM) uses electronic beam fusion, multi-jet fusion uses agent and energy fusion, and selective heat sintering (SHS) uses thermal fusion.

Various additive manufacture apparatus includes a production or build chamber in which devices are manufactured.

In powder bed fusion (PBF), a thin layer of powdered material is spread over a build platform contained in a production or build chamber. Next, the PBF printer or apparatus utilizes a heat source to selectively scan over and fuse the powdered material into a first cross-section of the part using a device data file. The build platform is then lowered by the thickness of the fused layer, and a new layer of powdered material is spread on the previously deposited fused layer. The process is repeated over and over again until the entire part or device is created. After forming all the layers of the part or device, the printed part or device is simply removed from the build platform and cleaned to undergo post-processing.

One consequence of this method of manufacture is that it takes a substantial period of time to fuse the number of layers necessary to produce an entire cranial remodeling orthosis device.

It is highly desirable to increase the throughput of manufacturing cranial remodeling orthosis devices. As described in detail hereinafter, new methods of manufacturing custom cranial remodeling orthosis devices utilizing additive manufacture have been developed.

In our new methods, the device data files of a plurality of cranial remodeling orthosis devices are nested together and fabricated concurrently, thereby increasing the throughput of the additive manufacture device. In some illustrative embodiments, the device data files for a cranial remodeling orthosis device may be arranged in one or more data arrays that include device data files for other cranial remodeling orthosis devices, and each of the data arrays is utilized to concurrently manufacture the corresponding device portions in a batch chamber In various illustrative embodiments, a plurality of custom cranial remodeling orthosis devices is concurrently manufactured by combining the device data files for the plurality of cranial remodeling orthosis devices into a nested data array and utilizing the nested data array to additively manufacture the plurality of cranial remodeling orthosis devices.

In other illustrative embodiments, a plurality of custom cranial remodeling orthosis devices is concurrently manufactured by partitioning the device data files for each of the plurality of custom cranial remodeling orthosis devices, forming a nested array of the partitioned device data files and printing the nested array. By forming a nested array of device data portions, a larger number of cranial remodeling orthotic devices or device portions can be manufactured in a concurrent print job.

Turning now to FIG. 1, a clinic 100 is shown that provides a point of service manufacturing apparatus for the manufacture of cranial remodeling orthosis devices. At this point of service manufacture clinic 100, an infant 101 that has plagiocephaly has a three-dimensional digital image captured of its head by digital capture apparatus 103. Digital capture apparatus 103 may be one of a known apparatus that is used to capture three-dimensional digital images of the entirety of a head. For example, digital capture apparatus 103 may use a laser or other beam emitting scanner of a type described in U.S. Pat. Nos. 6,572,572 and 6,340,353, both of which are assigned to the assignee of this invention. Digital capture apparatus 103 may alternatively comprise optical capture apparatus such as that described in U.S. Pat. Nos. 7,142,701, 7,162,075, 7,245,743, 7,280,682, 7,305,369, 7,542,950, 8,103,088, and 8,217,993 all of which are also assigned to the assignee of this invention. The disclosures of all the above-listed patents are incorporated herein in their entireties by reference.

Digital capture apparatus 103 processes the captured data and generates a captured head data file 105 for the subject's head. In addition, digital capture apparatus 103 or other apparatus processes data file 105 to generate a modified head data file 107. The head shape represented by modified head data file 107 represents a desired or corrected head shape for the subject. The methodology for generating the modified head shape data file is described in the above-identified patents and additionally in U.S. Pat. Nos. 8,442,288, 8,442,308, 8,472,686, 8,494,237, and 8,787,657 all of which are assigned to the assignee of this invention. The disclosures of these additional patents are incorporated herein in their entireties by reference.

The captured head data file 105 and modified head data file are both accessed by processor 109 executing program 111 to generate a device data file 113 that completely defines a custom cranial remodeling orthosis device for subject 101. The operation of processor 109 executing program 111 is described in detail herein below.

Device data file 113 is provided to an additive manufacture device 115. Additive manufacture device 115 utilizes device data file 113 to manufacture a custom cranial remodeling orthosis device 117 for subject 101.

Additive manufacture device 115, in various embodiments, is a commercially available three-dimensional printer that is operable to provide layers of material to form cranial remodeling device 117. It will be recognized by those skilled in the art that there are various types of additive manufacture devices that are commercially available as described hereinabove and the present invention encompasses those various types of additive manufacture devices.

In the embodiment shown in FIG. 1 digital capture apparatus 103 and additive manufacture device 115 are provided at the same physical location. Processor 109 may also be located at the same physical location or located remotely from the clinic 100 and data linked thereto to provide the effect of being located at clinic 100. In other embodiments, additive manufacture apparatus 115 may be located at a location separate from digital capture apparatus 103.

It will be further appreciated by those skilled in the art that although a single separate processor 109 is shown in FIG. 1, processor 109 is merely representative and may comprise one or more processors that are either located at clinic 100 or at a remote location or some combination thereof. Still further processor 109 may be incorporated into digital capture unit 103 such that the processor of digital capture unit also executes program 111 to generate device file 113.

Digital capture apparatus 103 operates on captured subject head data representing the digital image of the head of subject 101 to mathematically remove the subject's body and other extraneous information to establish a subject data file. The digital image of the subject's body is mathematically cropped or removed leaving just digital data representative of the digital image of the subject's head to provide three-dimensional cropped subject data.

The three-dimensional cropped subject data is oriented into a predetermined standardized orientation for further processing to produce a cropped and oriented data file that is referred to as the captured head data file 105.

It will be appreciated by those skilled in the art that in other embodiments, program 111 may provide the cropping and orientation functions that are provided by digital capture apparatus 103.

Processor 109, executing program 111, utilizes captured head data file 105 to generate curvature maps of the subject's head. A plurality of different types of curvature maps are generated by processor 109, executing program 111. Specific ones of the curvature maps are used to locate specific curvatures and features for a cranial remodeling device. Program 111 is utilized to create, reference, and cross-reference the curvature maps to determine an optimal position of a device contour.

The term "contour" or "contour lines" as used herein is the shape that defines the peripheral edges of the cranial remodeling device or what in the past has been called "trim lines" for cranial remodeling devices that were formed by first thermoforming foam and plastic layers onto a head model and then cutting or trimming the foam and plastic to a final shape of the cranial remodeling orthosis device to be worn on the head of a subject.

Program 111, executed by processor 109, identifies landmarks or features or curvatures to determine the contour of the cranial remodeling orthosis device.

In the embodiment described below, the cranial remodeling orthosis device comprises bottom and top contour lines 117*a*, 117*b*. The bottom contour line 117*a* and the top contour line 117*b* are each calculated for cranial remodeling orthosis device 117 by processor 109 executing program 111 operating on initially captured head data file 105.

Figure 2:
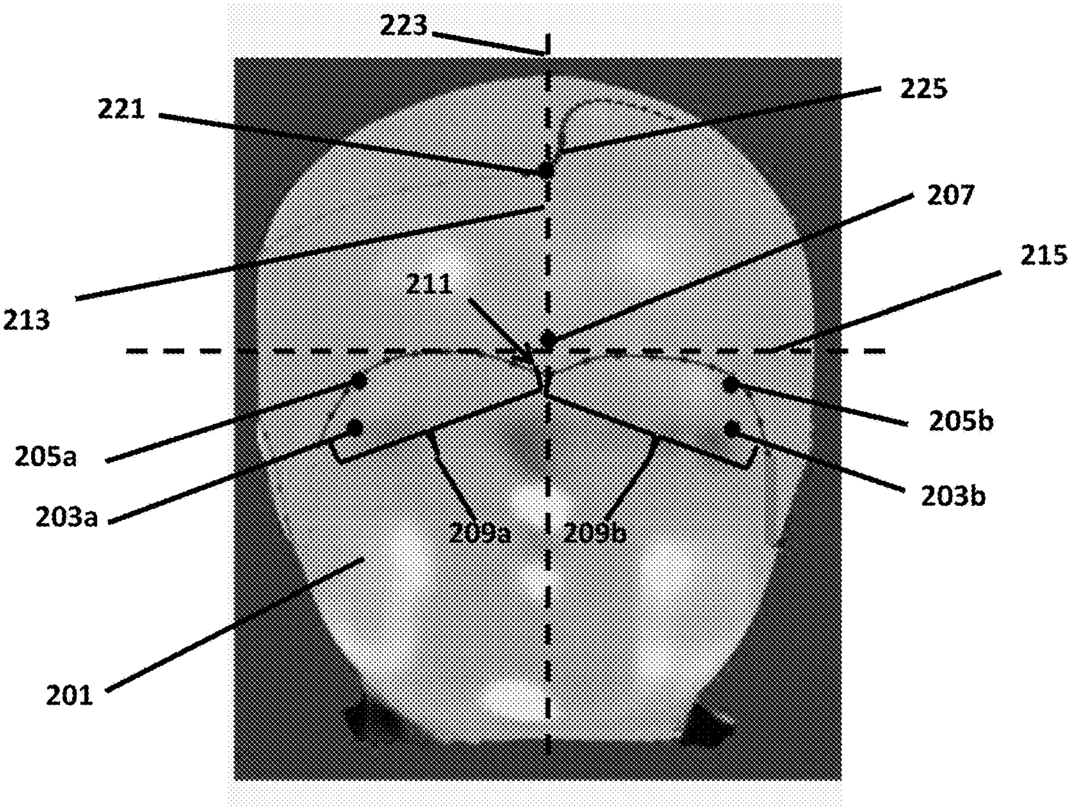
FIG. 2 is a screen shot of a frontal view of the head of a subject.
Figure 3:
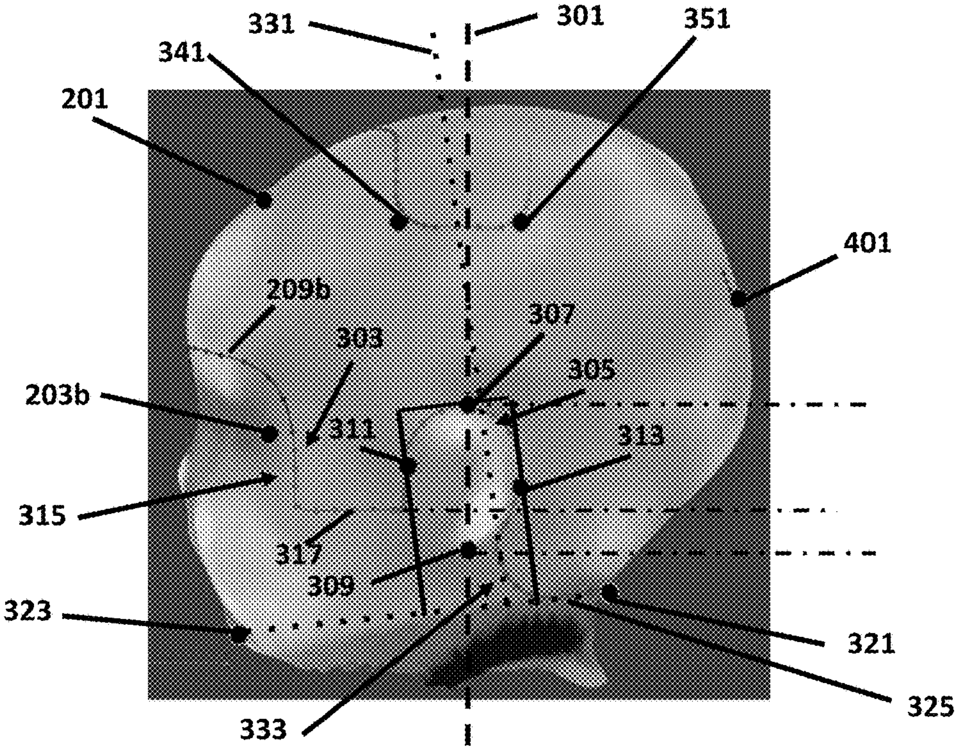
FIG. 3 is a screen shot of a left side view of the head of FIG. 2.

Turning now to FIGS. 2 and 3, execution of program 111 to calculate bottom contour line 117*a* is described herein below first and then the execution of program 111 to calculate top contour line 117*b* is described.

FIG. 2 illustrates a curvature map 201 of a frontal view head of subject 101. Program 111 is executable to determine a bottom anterior contour line segments or splines by first mathematically defining two exocanthion locations 203*a*, 203*b*, the two frontozygomatics points 205*a*, 205*b* on the head, and the *glabella* 207. Using these five points 203*a*, 203*b*, 205*a*, 205*b*, 207 as a spatial reference, an elliptical cylinder shape is used to create the orbit contour splines 209*a*, 209*b*.

Program 111, executed by processor 109, identifies the sagittal plane 215 and uses sagittal plane 215 to identify the location of a key portion 211 of cranial remodeling device 117. In the embodiment, program 111 as executed by processor 109 generates a contour for key portion 211. Key portion 211 dips a predetermined distance below an orbital horizontal that is identified by program 111.

Turning now to FIG. 3, program 111 as executed by processor 109 identifies a coronal plane 301 on the head and anterior temporal extension lines 303*a*, 303*b* are attached to the ends of the orbital splines 209*a*, 209*b* at the exocanthions 203*a*, 203*b* and continue down parallel to coronal plane 301.

Program 111, executed by processor 109, generates ear contours or splines 305 for each ear. The location of ear contours 305 are determined by mathematically defining the top ear points 307, bottom ear points 309, front ear points 311 and back of ear points 313 and connecting the points 307, 309, 311, 313 for each ear with a curved spline 315. In addition to determining the ear contours 305, the midway point of the total length of the ear is defined.

The location, size and shape of the temporal piece contours 315 are determined by using the mathematically defined exocanthion points 203*a*, 203*b* and front ear points 311. The location of the bottom 317 of the temporal contour 315 is a predetermined portion "x" of an ear's total length "y" above the bottom ear point 309.

Program 111, executed by processor 109, calculates a neck inflection portion of the contour. The location of the neck inflection contour portion is determined by using a mathematically defined neck inflection and the ears bottom points 309. The final location of the neck inflection point 321 is determined by calculating a weighted average between the mathematically defined neck inflection point and the ear bottom points 309.

Program 111, executed by processor 109, calculates an angle of the neck inflection contour is determined by calculating a guideline that connects the neck inflection point 321 to a chin point 323.

Program 111, executed by processor 109, calculates mastoid contours 331. The location, size and shape of the mastoid contours 331 are determined by using the mathematically defined ear points 307, 309, 311, 313, the neck inflection point 321 and chin point 323. A guideline 325 that connects the neck inflection point 321 to the chin point 323 is calculated. A line 331 perpendicular to the guideline 325 is placed a predetermined distance from the posterior ear point 313.

Curved contour portions 333 are each calculated, sized and positioned to be tangent to the back of the ear spline 305 and contact both the neck inflection point 321 to guide line 325 and line 331. The shape of each curved contour portion 333 is different for each head.

Cranial remodeling device 117 further comprises a top contour 117*b*.

Program 111, executed by processor 109, identifies a point 221 of low curvature on the sagittal midline 223 above the frontal bones as the location of an anterior superior contour.

Figure 4:
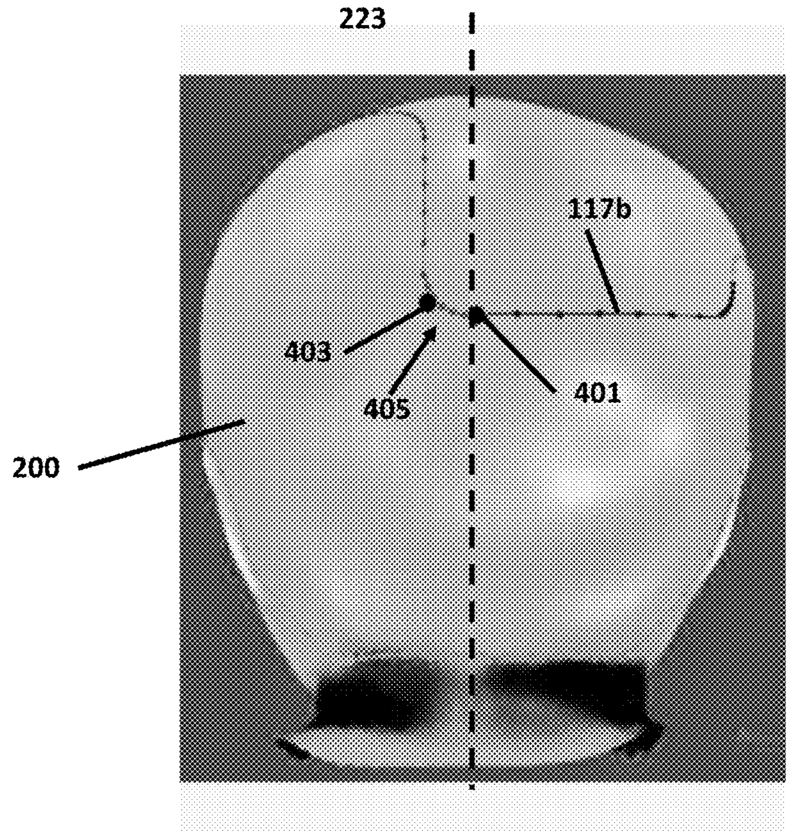
FIG. 4 is a screen shot of the rear of the head of FIG. 2.

Program 111, executed by processor 109, identifies a point 401 of low curvature on the sagittal plane 223 above the Occipital bones as the height location of the posterior superior as shown in FIG. 4.

Program 111, executed by processor 109, determines an anterior corner front starting point 225 from a standard offset of sagittal plane 223.

Program 111, executed by processor 109, determines an anterior corner lateral starting point 341 in the coronal direction utilizing curvatures associated with the coronal suture.

Program 111, executed by processor 109, determines a posterior corner back starting point 405 in the sagittal direction by calculating a standard offset of the mathematically derived sagittal plane 223.

Program 111, executed by processor 109, determines a posterior corner lateral starting point 351 in the coronal direction using the curvatures associated with the coronal plane 301.

Figure 5:
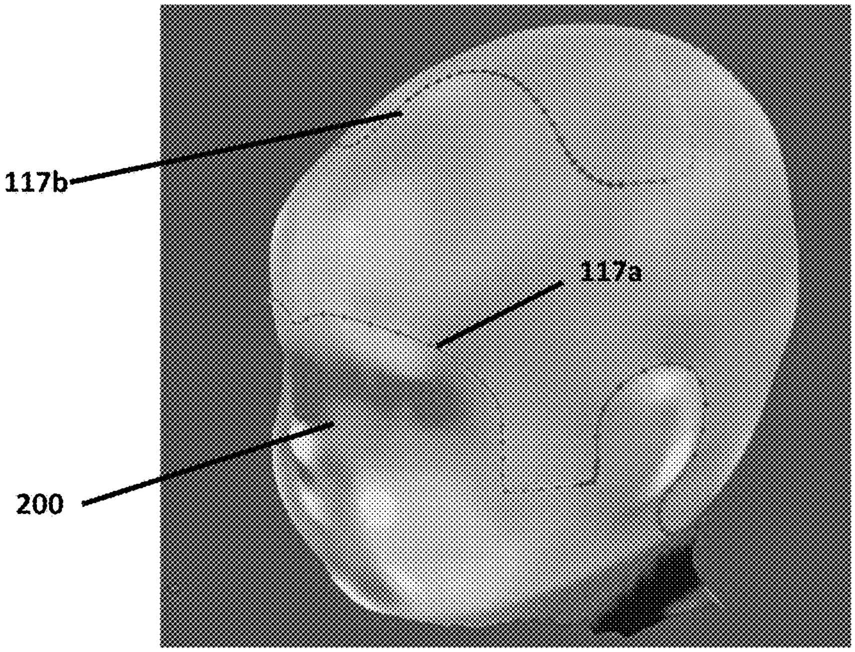
FIG. 5 is a screen shot of a perspective view of the head of FIG. 2 having contour lines thereon.

Program 111, executed by processor 109, by performing the above calculations and operations, defines top contour 117*b* and bottom contour 117*a* on the oriented head shape as shown in drawing figures and most clearly shown in FIGS. 1 and 5.

Figure 6:
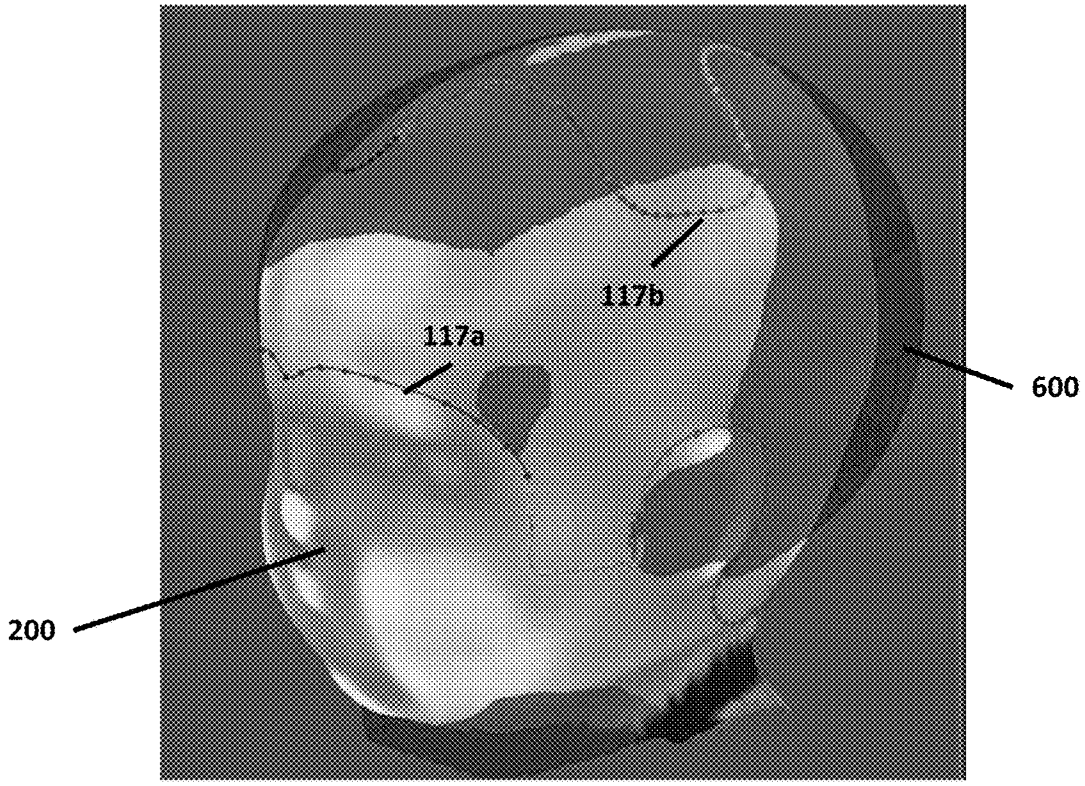
FIG. 6 is a screen shot of the perspective view of the head as shown in FIG. 5 having a modified head shape juxtaposed thereon.

Once the top and bottom contours 117*b*, 117*a* are created on the unmodified head shape, program 111, executed by processor 109, juxtaposes modified head shape 600 onto unmodified head shape 200 as shown in FIG. 6.

Program 111, executed by processor 109, utilized modified head shape 600 to generate a multilayered cranial remodeling device 700 juxtaposed onto modified head shape 600. At this point, multilayered cranial remodeling device 700 extends over substantially all of modified head shape 600 as shown in FIG. 7.

Figure 7:
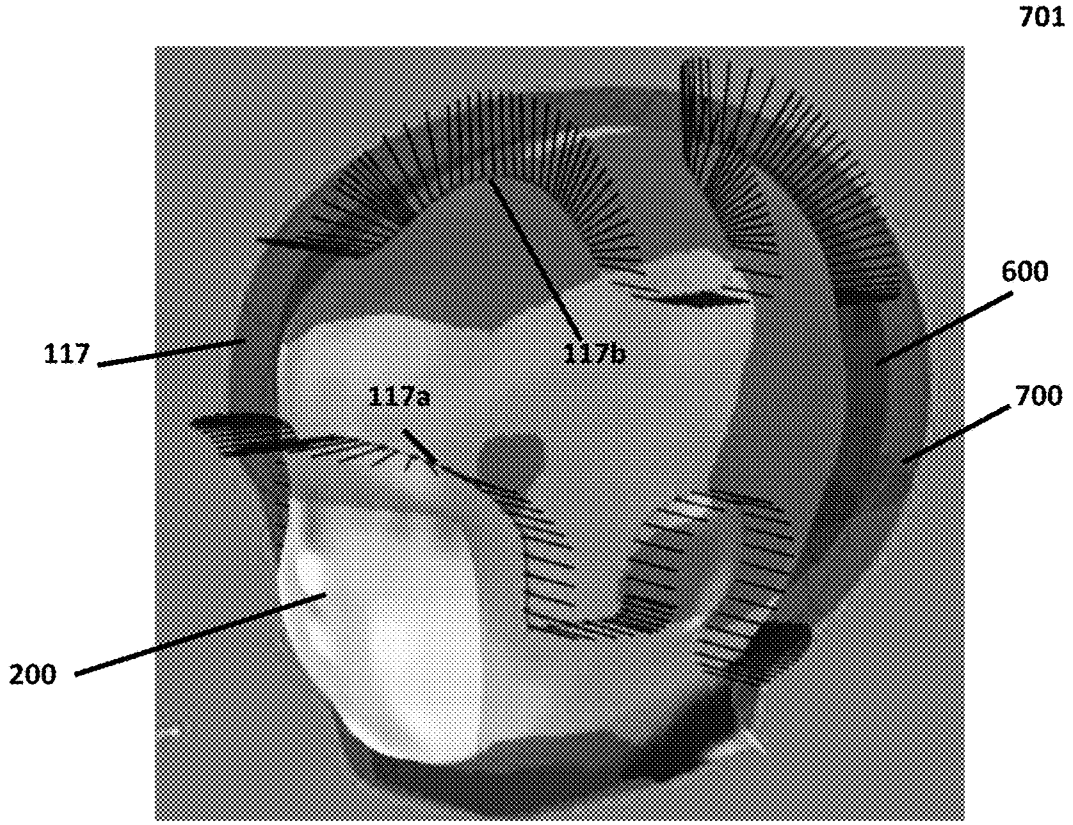
FIG. 7 is a screen shot of the perspective view of FIG. 6 further having an image of a cranial remodeling device thereon and lines projecting from the contour lines through the cranial remodeling device.

Program 111, executed by processor 109, projects lines 701 from top contour 117*b* and bottom contour 117*a* through juxtaposed modified head shape 600 and through juxtaposed multilayer cranial remodeling device 700 as shown in FIG. 7.

Figure 8:
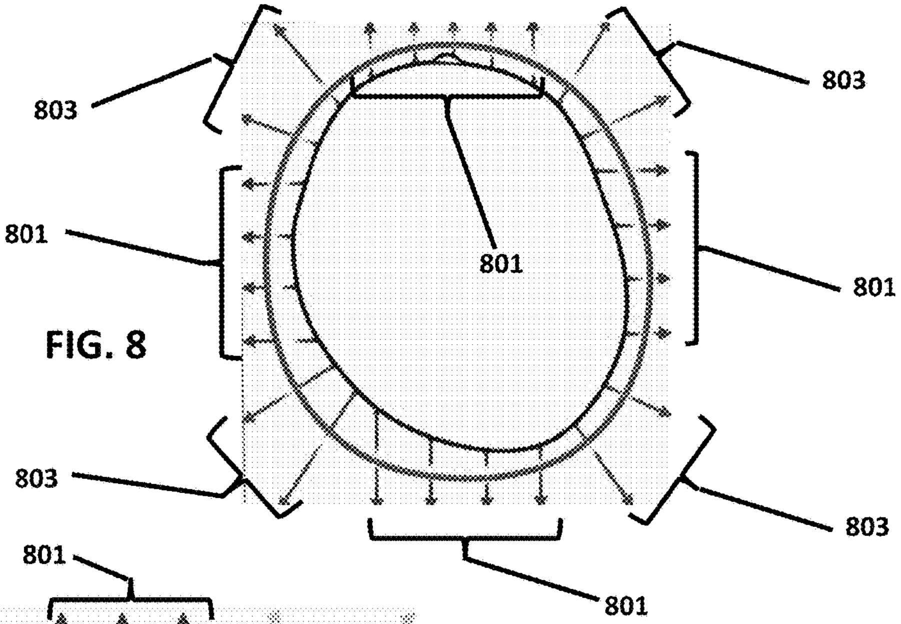
FIGS. 8, 9, and 10 illustrate the direction of the projecting lines of FIG. 7 from a top view, left side view and frontal view respectively.
Figure 9:
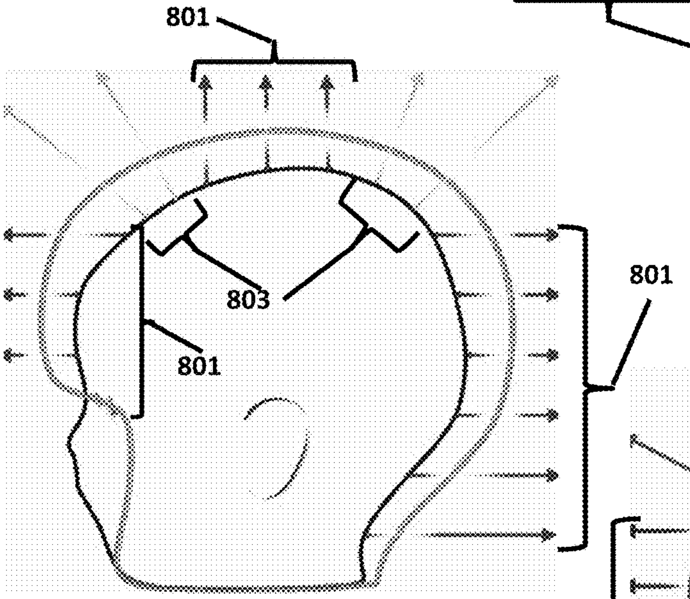
Figure 10:
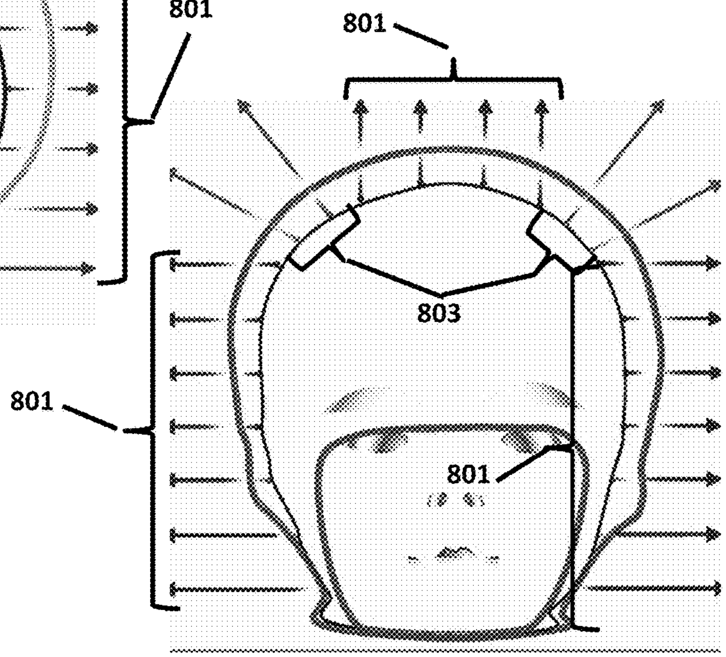

Lines 701 are projected from unmodified head shape 200. As shown in FIGS. 8, 9, and 10, to maintain an optimal relationship to the modified head shape 600, lines 701 are projected directly right and left for lateral contours 801 and front/back for anterior and posterior contours 803. Where the right and left lines transition to the front and back lines 805 the projection of the lines is radial.

Program 111, executed by processor 109, utilizes projected lines 701 to define bottom and top contours 117*a*, 117*b* onto multilayered cranial remodeling device 700 to generate a device file 113.

In generating device file 113, program 111, executed by processor 109, selects the properties of each of a plurality of layers for the cranial remodeling device 117.

Figure 11:
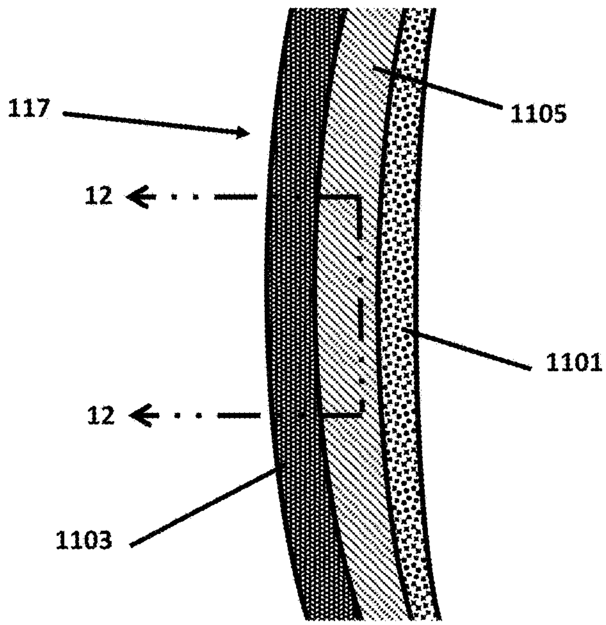
FIG. 11 is a cross section through a portion of an embodiment of a cranial remodeling device.

Additive manufacture device 115 of FIG. 1 utilizes device file 113 to manufacture a cranial remodeling device by depositing a plurality of layers as shown in FIG. 11. FIG. 11 is a cross-section of a portion of a cranial remodeling device 117 and is intended to be representative of embodiments of such a device. Other embodiments may have more or less layers deposited by additive manufacture.

Various embodiments of a custom cranial remodeling orthosis device 117 to correct a deformed head of a subject comprise an inner layer 1101 shaped to contact the head of the subject at predetermined areas. The inner layer 1101 is deposited by additive manufacturing device 115 shown in FIG. 1. Cranial remodeling device 117 comprises an outer layer 1103 deposited by the additive manufacturing device 115. The inner layer 1101 and the outer layer 1103 are each formed by the additive manufacture device utilizing device data file 113 derived from a subject or captured head data file 105. The subject data file 105 is representative of the shape of the deformed head of the subject 101.

Device data file 113 determines the shape of the cranial remodeling device 117 to correct the shape of the deformed head.

In various embodiments, device data file 113 is derived from subject data file 105 and a modified data file 107. The modified data file 107 is representative of a modified head shape.

Device data file 113 is derived by one or more processors 109 operable to provide: determining contour lines 117*a*, 117*b* for custom cranial remodeling device 117*e* on the deformed head shape 200 shown in FIGS. 2 through 10; juxtaposing a digital representation 600 of the modified shape on the deformed head shape 200 as shown in FIGS. 6 and 7; projecting the contour lines 117*a*, 117*b* outward from the deformed head shape 200 onto the modified shape 600; and utilizing the contour lines to produce the device data file 113.

In various embodiments the inner layer comprises portions positioned to contact the head at predetermined surface areas of the head. It will be appreciated by those skilled in the art that contact with the head may be direct or indirect where, for example, a liner is included within the cranial remodeling orthosis device.

In various embodiments, inner layer 1101 comprises a plurality of separate portions that are not shown in the drawing figures. Each separate portion of inner layer 1101 is configured to contact one of a corresponding plurality of areas on the head shape 200.

In various embodiments in which fusion bed additive manufacturing is not utilized, cranial remodeling device 117 comprises one or more removable manufacturing supports, that are not shown in the drawing figures, to facilitate additive manufacture of custom cranial remodeling device 117. The supports are provided solely to facilitate additive manufacture and are removed prior to utilization of cranial remodeling device 117. The supports may be of any convenient configuration and may be comprised from an additive material that is easily dissolved or is otherwise easily removable from the finished cranial remodeling device.

In various embodiments, inner layer 1101, outer layer 1103 and intermediate layer 1105 each comprise one or both of different strength and material properties. Device data file 113 as generated by processor 109 executing program 111 automatically determines the material deposited for each layer 1101, 1103, 1105 and any configuration details for each layer 1101, 1103, 1105.

In various embodiments, cranial remodeling device 117 comprises alignment marks deposited on the cranial remodeling device 117 by additive manufacture device 115. The alignment marks aid a clinician in fitting custom cranial remodeling device 117 to subject 101. The alignment marks may be formed by incorporation of various landmarks such as depressions or protrusions or other identifications formed into a layer and visible to a clinician.

Various embodiments comprise a plurality of different layers comprising inner layer 1101, outer layer 1103 and one or more intermediate layers 1105, the plurality of layers comprising one or more of different strength properties, material properties, and configurations, each layer 1101, 1103, 1105 of the plurality of layers is deposited by the additive manufacturing device.

Figure 12:
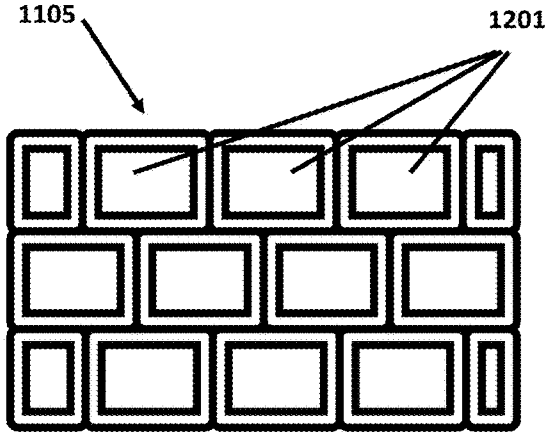
FIG. 12 is a cross section of a cranial remodeling device taken along lines 12-12 of FIG. 11.

In various embodiments, at least one layer of the plurality of layers comprises a cellular configuration as shown in FIG. 12. Although a rectangular cellular construction is shown in FIG. 12, it will be understood by those skilled in the art, that various configurations may be selected. By way of non-limiting example, the cellular construction may present a beehive cellular construction. The use of a cellular construction may present particular advantages for certain embodiments. For example, the use of a cellular construction may provide greater strength and a lighter weight cranial remodeling device. Also, the cellular construction may be varied throughout a cranial remodeling orthosis device such that, when the cranial remodeling device is worn, different pressure levels may be maintained on different regions of the wearers head to facilitate controlled growth of the head to a corrected head shape as the wearer grows.

In at least one embodiment, at least one layer of the plurality of layers comprises carbon fibers integrated therein. For example, outer layer 1103 may comprise carbon fibers to provide greater strength and lighter weight to cranial remodeling device 117.

By utilizing additive manufacture, one or more electronic sensors may be embedded in cranial remodeling device 117 as part of the additive manufacture protocol presented by device data file 113.

The one or more electronic sensors may be operable to determine pressure levels applied to the subject's head when custom cranial remodeling device 117 is worn.

The one or more electronic sensors may further be operable to confirm that custom cranial remodeling device 117 is being correctly worn on the subject's head.

In other embodiments one or more electronic transducers are manufactured into the custom cranial remodeling device 117 by the additive manufacture device 115. The one or more electronic transducers may be useable to determine one or more of tilt and turn of the subject's head, whether the custom cranial remodeling device 117 is being worn, and the frequency of predetermined head motions.

Various embodiments may comprise components integrally formed with the custom cranial remodeling device 117 by the additive manufacture device 115. The components may comprise one or more of apparatus for fastening the cranial remodeling device in place on the head, electronic transducers, and electronic sensors.

Although the embodiments described above and herein below are for custom cranial remodeling devices 117, other embodiments may be for custom headwear devices to be worn on the head of a subject. Embodiments of custom headwear devices may comprise: an inner layer 1101 shaped to contact the head of the subject at predetermined areas, the inner layer deposited by an additive manufacturing device; an outer layer 1103 deposited by the additive manufacturing device. The inner layer 1101 and the outer layer 1103 are each formed by the additive manufacture device 115 utilizing a device data file 113 derived from a subject or captured head data file 105. The subject data file 105 is representative of the shape of the head.

In various embodiments of the custom headwear device, the device data file is derived by one or more processors 109: determining contour lines 117*a* for the custom headwear device 117 on the head shape 200 utilizing device data file 113; projecting the contour lines 117*a* outward from the head as shown in FIG. 7; and utilizing the contour line 117*a* to produce the device file. It will be apparent to those skilled in the art that if the custom headwear device 117 is not intended to be utilized for cranial remodeling but, for example, is intended to be utilized as a protective headwear device, there is no modified head shape 600 and the shape of the protective headwear device 700 is juxtaposed directly onto the subject head shape 200. The contour lines 117*a* are then projected outward as shown in FIG. 7 to provide contour lines for the protective headwear device and to generate the corresponding custom headwear device data for use by additive manufacture device 115.

In various embodiments of the custom headwear device 117, inner layer 1101 comprises portions positioned to contact the head at predetermined surface areas of the head.

In various embodiments of the custom headwear device, inner layer 1101 may comprise a plurality of separate portions, each portion configured to contact one of a corresponding plurality of areas on the subject's head.

In various embodiments of the custom headwear device 117, one or more removable manufacturing supports as described herein above are deposited to facilitate additive manufacture of the custom headwear device.

Various embodiments of the custom headwear device 117 comprise at least one intermediate layer 1105 between the inner layer 1101 and the outer layer 1103, the intermediate layer 1105 is deposited by the additive manufacturing device.

In various embodiments of the custom headwear device 117, the inner layer 1101, the outer layer 1103, and the intermediate layer 1105 each comprise one or both of different strength and material properties.

Various embodiments of the custom headwear device 117 comprise alignment marks as described herein above.

Various embodiments of the custom headwear device 117 comprise guidelines printed by the additive manufacture device on the custom headwear device as described herein above.

Various embodiments of the custom headwear device comprise a plurality of different layers comprising inner layer 1101, outer layer 1103, and one or more intermediate layers 1105, the plurality of layers comprising one or more of different strength properties, material properties, and configurations.

In various embodiments of the custom headwear device 117, at least one layer 1105 of the plurality of layers comprises a cellular configuration as shown in FIG. 12 and as described herein above.

In various embodiments of the custom headwear device 117, at least one layer of the plurality of layers comprises carbon fibers integrated therein.

Various embodiments of the custom headwear device 117 may comprise one or more electronic sensors manufactured by the additive manufacture device into the custom headwear device.

Various embodiments of the custom headwear device comprise one or more electronic sensors operable to determine pressure levels applied to the head when the custom headwear device is worn on the head; and the one or more electronic sensors are manufactured into the custom headwear device by the additive manufacture device.

Various embodiments of the custom headwear device 117 comprise one or more electronic transducers manufactured into the custom headwear device by the additive manufacture device.

In various embodiments of the custom headwear device 117, the one or more electronic transducers are useable to determine one or more of tilt and turn of the head, whether the custom cranial remodeling device is being worn, and the frequency of predetermined head motions.

Various embodiments of the custom headwear device comprise components integrally formed with the custom cranial remodeling device by the additive manufacture device; and the components comprise one or more of apparatus for fastening the cranial remodeling device in place on the head, electronic transducers, and electronic sensors.

In various embodiments, the methods and apparatus described for manufacture of cranial remodeling devices may also be used to manufacture custom headwear devices for subjects such as, by way of non-limiting example, sports helmets and protective helmets. In the manufacture of custom headwear devices, contour lines may be calculated on a captured subject data file representative of the shape of the subject's head that is captured utilizing one of digital image capture apparatus and scanning apparatus. The contour lines may be extended outward from the contour lines on the head image data representative of the subject's head through a calculated multi-layered headwear device juxtaposed onto the subject's head image data as described herein above.

Figure 25:
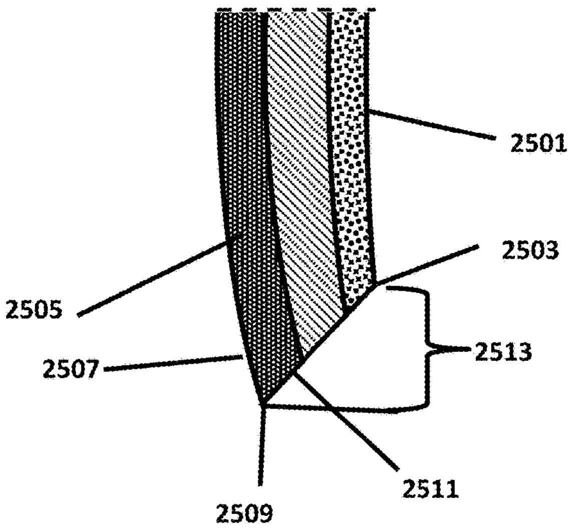
FIG. 25 located on the same page as FIG. 11 is a cross-section of an edge portion of a cranial remodeling orthosis device.

Turning now to FIG. 25 which appears on the same drawing sheet as FIG. 11, the peripheral edge of one embodiment of a custom cranial remodeling orthosis is shown. The cranial remodeling orthosis device has an inner layer carrying an inner surface 2501 shaped to provide modification of said shape of said deformed head. Inner surface 2501 carries an inner surface peripheral edge 2503. An outer layer 2505 has an outer surface 2507 carrying an outer surface peripheral edge 2509. Inner surface 2501 and said outer surface 2507 each comprise a shape determined from a device data file. At least one of the inner surface peripheral edge 2503 and said outer surface peripheral edge 2509 is determined from contour lines from one or more of curvatures, features, and reference points on said shape of said deformed head as described herein above. The inner surface peripheral edge 2503 and outer surface peripheral edge 2509 are offset from each other. Offset 2513 produces a beveled or tapered surface 2511.

In some embodiments, the offset 2513 between the inner surface peripheral edge 2503 and the outer surface peripheral edge 2509 is uniform along the entirety of the inner surface peripheral edge 2503 and outer surface peripheral edge 1509.

In some embodiments, the inner surface peripheral edge and the outer surface peripheral edge are carried on an inferior portion of the cranial remodeling orthosis device and beveled surface 2511 is carried on the inferior portion.

An inner surface peripheral edge 2503 and an outer surface peripheral edge 2509 may also be carried on a superior portion of the cranial remodeling orthosis edge and a beveled surface 2511 is also carried on the superior portion.

The offset 2513 on the superior portion may also be uniform along the entirety of superior inner surface peripheral edge 2503 and superior outer surface peripheral edge.

Providing an offset between the inner edge 2503 and the outer edge 2509 is advantageous in some embodiments to enhance wearing of the cranial remodeling orthosis device as well as putting the orthosis device on and removing it.

As pointed out hereinabove, when manufacturing cranial remodeling orthosis devices utilizing additive manufacture apparatus, manufacturing throughput becomes limited by the length of time to print the devices.

Where a plurality or large number of cranial remodeling orthosis devices are to be manufactured, manufacture of such devices one at a time is not an efficient approach.

New methods of manufacturing a plurality of cranial remodeling orthosis devices have been developed that significantly increase manufacturing throughput. The methods utilize cranial remodeling orthosis device data files. These device data files, as described hereinabove define the shape of a corresponding custom cranial remodeling orthosis device including contour lines defining its peripheral edges. In the methods, a first plurality of cranial remodeling orthosis device data files is received or generated by processor 109 shown in FIG. 1 or one or more other processors.

Figure 14:
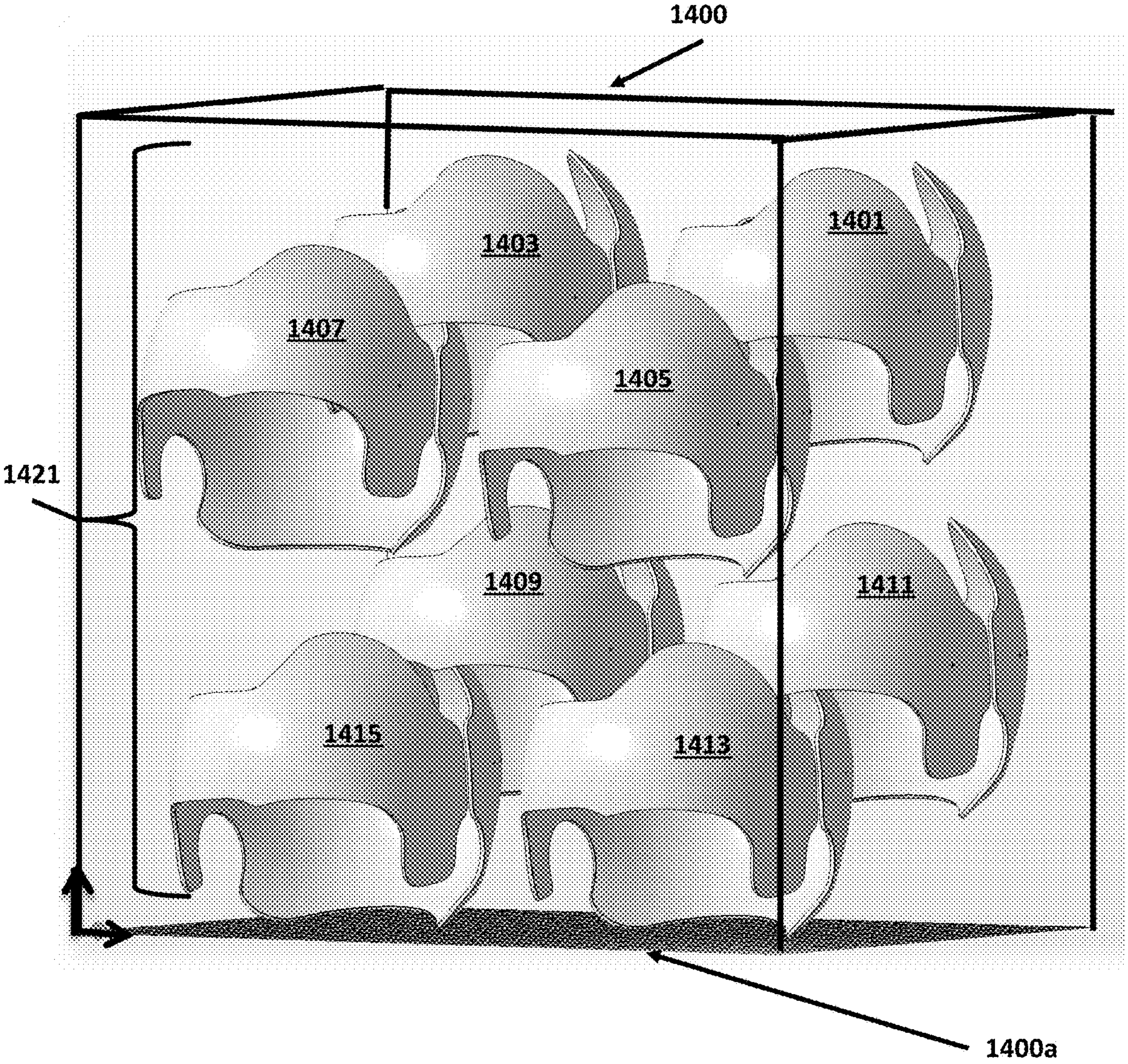
FIG. 14 is an isometric view of concurrent additive manufactured cranial remodeling orthosis devices.

Processor 109 or one or more other processors utilizes received first plurality of cranial remodeling orthosis device data files to generate a nested array device data file comprising a plurality of cranial remodeling orthosis device data files arranged in a nested array. The nested array device data file is arranged for concurrent manufacture of corresponding nested array 1421 of cranial remodeling orthosis devices as shown in FIG. 14 by additive manufacture apparatus as shown in a production or build chamber 1400.

Processor 109 or one or more other processors utilizes predetermined selection criteria to select a plurality of cranial remodeling orthosis device data files from the first plurality of cranial remodeling orthosis device data files for inclusion into the nested array device data file.

There are several reasons for using selection criteria. In many instances, the age of the patient is important to consider. For example, if the patient is older, it is important to get the patient into a cranial remodeling orthosis device as soon as possible while the head is still growing. In other instances, it is important to get a very young patient into a cranial remodeling orthosis device as soon as possible to take advantage of the rapid growth at younger ages.

Other criteria that may be used alone or in combination with age criteria is the geographic location or shipping zone to where cranial remodeling orthosis devices are to be sent for shipping efficiency and to reduce shipping costs. It may be advantageous to concurrently manufacture a group of cranial remodeling orthosis devices that are to be shipped to the same clinic.

Still further criteria to consider include the date of receipt or sending of cranial remodeling orthosis device data files.

Additional selection criteria that may be considered are the sizes of the cranial remodeling orthosis devices and the types of such devices.

It will be appreciated by those skilled in the art that multiple ones of the various selection criteria may be utilized in selecting cranial remodeling orthosis files for inclusion into a nested array data file for concurrent manufacture. In addition, it will be appreciated by those skilled in the art that other criteria may be utilized alone or in combination with the various criteria described above.

One or more algorithms may be executed on processor 109 or on one or more other processors to utilize predetermined criteria to select cranial remodeling orthosis device files for inclusion into a nested array data file. These algorithms in addition to applying predetermined criteria may be utilized to select and position the cranial remodeling orthosis device data files into a nested matrix array to optimize and/or maximize the number of cranial remodeling orthosis devices and/or device portions that are concurrently manufactured in the volume of production or build chambers of the additive manufacture apparatus being utilized.

The method may comprise utilizing one or more algorithms to select the plurality of device data files for concurrent manufacture from a first plurality of device data files utilizing selection criteria and utilizing one or more second algorithms to arrange the plurality of device data files into a nested array.

By forming nested arrays of cranial remodeling orthosis device files, corresponding arrays of pluralities of cranial remodeling orthosis devices and/or device portions are concurrently manufactured, thereby increasing manufacturing throughput.

In addition to forming nested arrays of cranial remodeling orthosis device data files, further improvements to increasing manufacturing throughput may be obtained by partitioning cranial remodeling orthosis device data files into portions to forming cranial remodeling orthosis device portion data files corresponding to cranial remodeling orthosis device portion. One or more algorithms are used to combine the device portion data files into a nested matrix array of cranial remodeling device portion data files. The nested array of cranial remodeling device portions may be utilized to concurrently manufacture a corresponding matrix array of cranial remodeling device portions. The manufactured cranial remodeling orthosis device portions are then assembled into cranial remodeling orthosis devices.

By partitioning the device data files into device data file portions and forming one or more nested arrays with the device data file portions, the number of cranial remodeling orthosis devices and/or device portions that are concurrently manufactured is increased thereby increasing the manufacturing throughput.

In various embodiments, the cranial remodeling orthosis device portions correspond to one or more anterior and one or more posterior portions of a cranial remodeling orthosis device. In other embodiments, the cranial remodeling orthosis device is partitioned into or one or more superior portion and one or more inferior portions.

In addition to partitioning cranial remodeling orthosis device data files to provide cranial remodeling device portions, connecting portions are added into each cranial remodeling orthosis device portion data file to facilitate assembly of the device portions into corresponding cranial remodeling orthosis devices.

Prior to concurrent manufacture of cranial remodeling orthosis devices, subject identification information is added to each cranial remodeling orthosis device data file. Corresponding subject identification information is included on each manufactured cranial remodeling orthosis device such that each custom cranial remodeling orthosis device may be correctly provided to the proper patient. In addition, in those embodiments wherein each cranial remodeling orthosis device data file is partitioned, subject identification information is provided in each partitioned portion so that subject identification information is included on each manufactured portion. It will be appreciated by those skilled in the art that subject identification information may be coded information or other information that may correlate to a patient's identity without specifying the exact identity of the patient.

Figure 13:
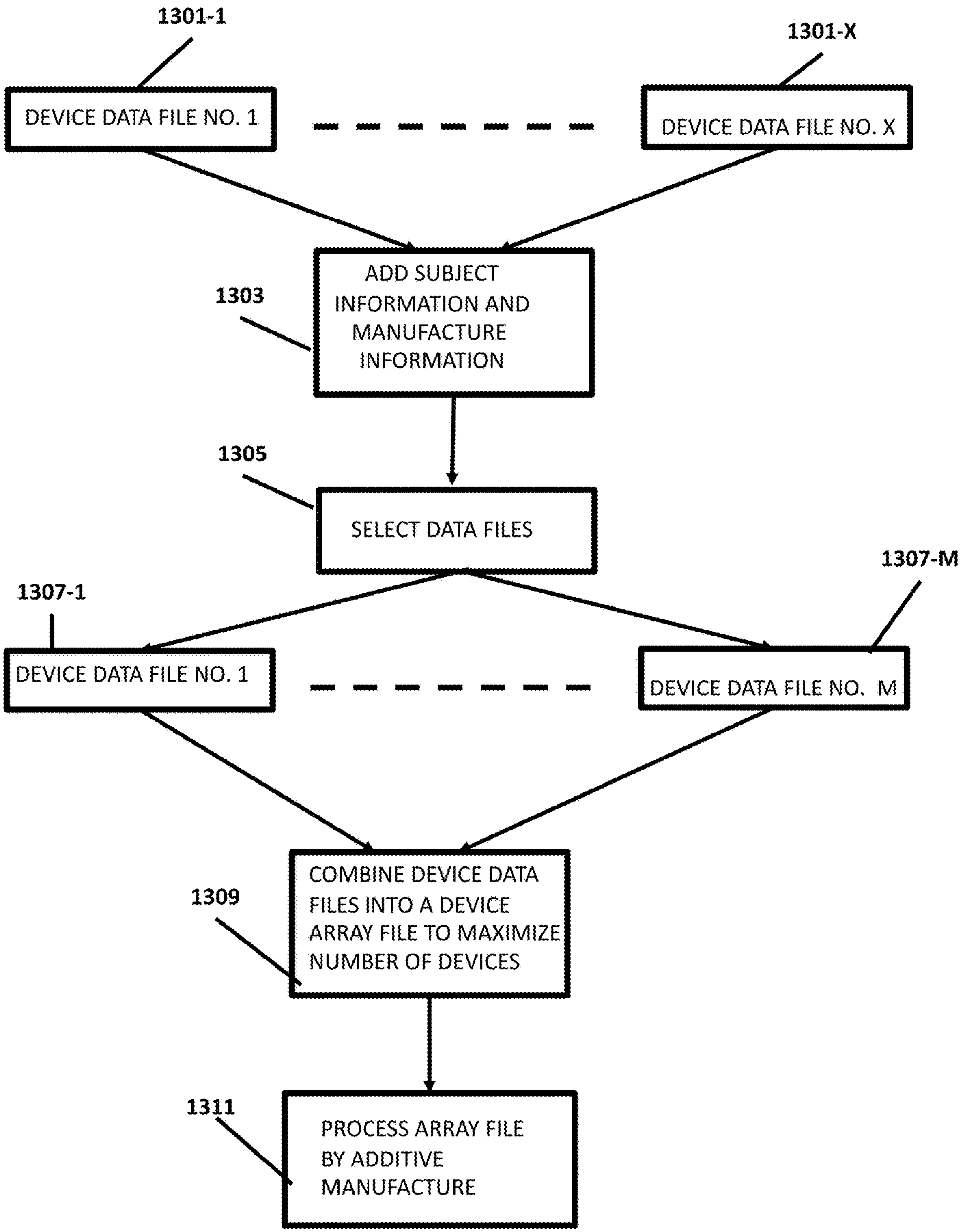
FIG. 13 is a flow chart of concurrent manufacture of cranial remodeling orthosis devices by additive manufacture.

FIG. 13 illustrates the methodology in creating a matrix array of a plurality of cranial remodeling orthosis device data files.

To provide concurrent manufacture of a plurality of custom cranial remodeling devices, a processor, which may be processor 109 in FIG. 1 or one or more other processors, receives a plurality of cranial remodeling orthosis device data files, each derived from a corresponding subject data file. As shown in FIG. 13, after a plurality of device data files 1301-1 through 1301-X are received, processor 109 or one or more other processors adds information into device data files 1301-1 through 1301-X at step 1303. If each of the device data files 1301-1 through 1301-X does not already include corresponding subject identification information, processor 109 adds subject identification into each device data file 1301-1 through 1301-X. In addition, processor 109 may add additional information into device data files 1301-1 through 1301-X comprising other relevant information such as manufacturing trace information comprising, for example, manufacturing data such as date of manufacture and batch information or a unique code that may be used to identify corresponding manufacturing data, e.g., lot number of material, serial number of printer etc.

At step 1305, processor 109 or one or more other processors utilizes one or more algorithms to apply predetermined selection criteria to the first plurality of device data files 1301-1 through 1301-X to select a plurality of device data files 1307-1A through 1307-XA. Device data files 1307-1A through 1307-XA are selected according to the predetermined criteria and to maximize the number of cranial remodeling orthosis devices that may be concurrently manufactured in a production or build chamber of a specified additive manufacture unit.

Processor 109 or one or more other processors combines device data files 1307-1A through 1307-XA to produce a nested device data file array at step 1309. The nested device data file array at step 1309 is configured to maximize the number of custom cranial remodeling devices that can be processed at step 1311 by additive manufacture apparatus.

The type of additive manufacture apparatus that may be used to process the device data file array may be any one of a number of commercially available additive manufacture units. Common among the various commercially available additive manufacture units is inclusion of production or build chamber of a defined volume in which devices are additively manufactured.

In FIG. 14, a production or build chamber 1400 for a fusion bed additive manufacture printer is shown. It will be appreciated by those skilled in the art, that the production or build chamber 1400 may have a different shape or configuration. It will also be appreciated by those skilled in the art, that the present invention is not limited to use of a fusion bed additive manufacture type apparatus. Details of the additive manufacture apparatus in the various embodiments are not shown for purposes of clarity. Chamber 1400 includes a defined volume in which a device or devices can be additively manufactured.

In the embodiment of FIG. 14, production or build chamber 1400 includes a bed 1400*a* through which material is provided for each of the multitude of layers of material that are fused into the desired device or devices. In the example shown in FIG. 14, nested device data file array produced at step 1309 comprising cranial remodeling orthosis device data files 1307-1A through 1307-XA is additively manufactured into a corresponding nested cranial orthosis device array 1421 comprising a plurality of cranial remodeling orthosis devices 1401, 1403, 1405, 1407, 1409, 1411, 1413, 1415.

In the embodiment of FIG. 14, the number of cranial remodeling orthosis devices concurrently manufactured in chamber 1400 totals eight in number. Considering that prior art approaches to manufacture custom cranial remodeling orthosis devices would manufacture one device at a time in build chamber 1400, the manufacturing throughput in this embodiment is increased eightfold by arranging device data files from eight custom cranial remodeling orthosis devices into a nested cranial remodeling orthosis device data array for manufacture into the corresponding nested cranial remodeling orthosis device array 1421.

It will be appreciated by those skilled in the art that the number of custom cranial remodeling devices concurrently manufactured depends on the selection criteria applied to the cranial remodeling orthosis device data files 1301-1 through 1301-X as well as the size of the particular additive manufacture device production or build chamber. The selection of the number of custom cranial remodeling devices to be included into a nested device data array 1421 will depend on the volume of production or build chamber 1400. Throughout the descriptions of various embodiments that follows, it is assumed that the volume and dimensions of chamber 1400 is constant for comparison purposes.

Processor 109 or one or more other processors selects a position and orientation for each device data file 1307-1A through 1307-XA in the nested device data file array produced at step 1305. The positions and orientations for the device data files are selected in accordance with one or more algorithms that selects the position and orientation of the various device data files 1307-1A through 1307-XA to optimize and/or maximize the number of custom cranial remodeling devices that can be concurrently manufactured in production or build chamber 1400.

Although concurrent manufacturing an array of eight custom cranial remodeling devices 1401, 1403, 1405, 1407, 1409, 1411, 1413, 1415 is a significant improvement over manufacturing one custom cranial remodeling device at a time, further significant improvements in manufacturing throughput may be provided.

By partitioning each custom cranial remodeling device and forming a nested array of the partitioned portions, a greater number of cranial remodeling orthosis devices may be concurrently manufactured.

Figure 15:
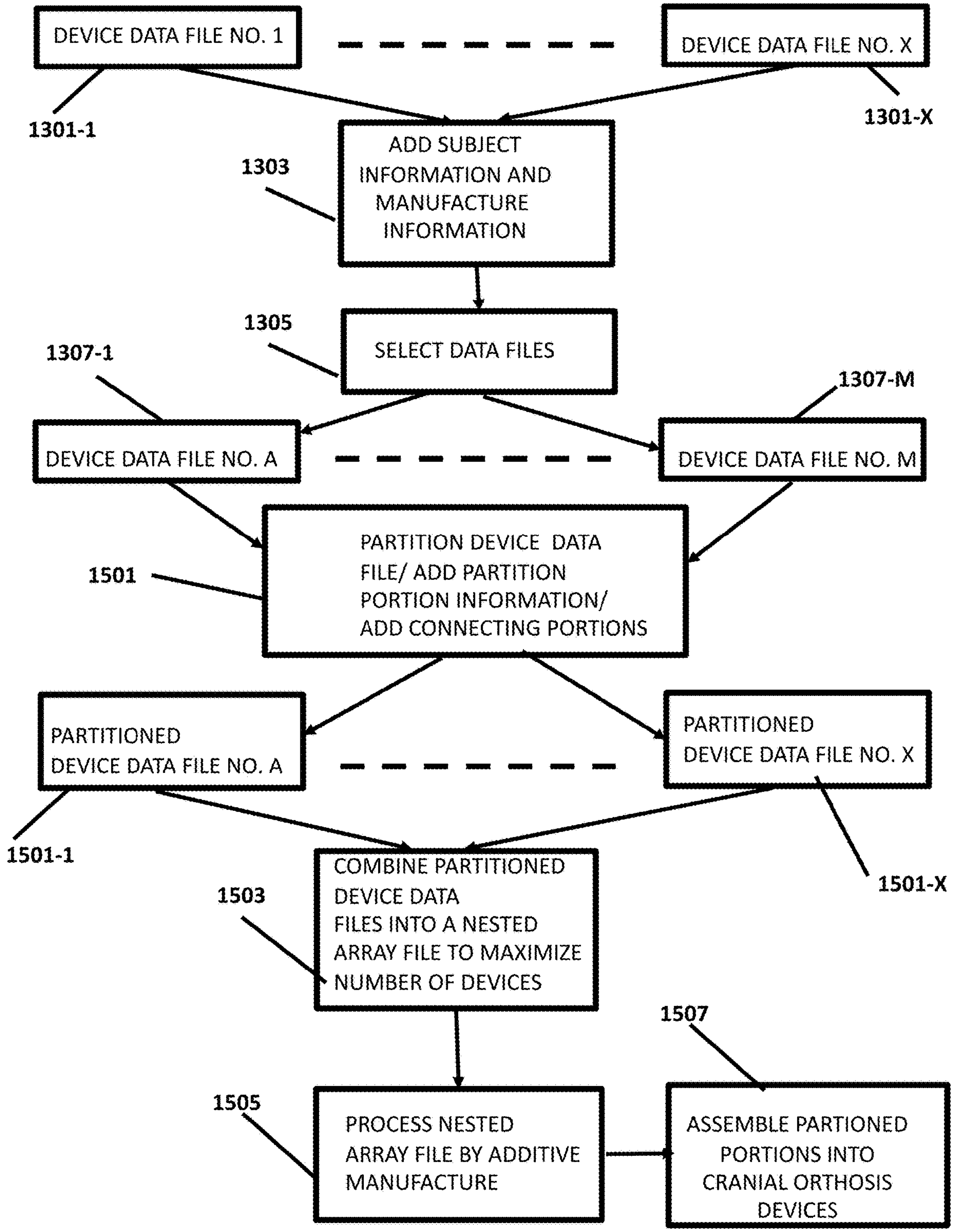
FIG. 15 is a flow chart of concurrent manufacturing of partitioned cranial remodeling orthosis devices.

Turning to FIG. 15, an embodiment of a method of concurrent manufacture of a plurality of partitioned custom cranial remodeling devices is shown. In the method of FIG. 15, a processor, which may be processor 109 in FIG. 1 or another processor or processors, receives a plurality of device data files 1301-1 through 1301-X, each derived from a corresponding subject data file. As shown in FIG. 13, after the plurality of device data files 1301-1 through 1301-X are received, processor 109 or another processor adds information into device data files 1301-1 through 1301-X at step 1303. If each of the device data files 1301-1 through 1301-X does not already include corresponding subject identification information, processor 109 adds subject identification into each device data file 1301-1 through 1301-X. In addition, processor 109 may add additional information into device data files 1301-1 through 1301-X comprising other relevant information such as manufacturing trace information comprising, for example, manufacturing data such as date of manufacture, batch information and a machine identifier or a unique code that may be used to identify corresponding manufacturing data.

At step 1305, processor 109 or one or more other processors utilizes one or more algorithms to apply predetermined selection criteria, as described herein above, to the first plurality of device data files 1301-1 through 1301-X to select a plurality of device data files 1307-1A through 1307-XA. Device data files 1307-1A through 1307-XA are selected according to the predetermined criteria and to maximize the number of cranial remodeling orthosis devices and/or device portions that may be concurrently manufactured in a production chamber of a specified additive manufacture unit.

At step 1501, one or more algorithms are utilized to partition each selected cranial orthosis device data file 1307-1A through 1307-XA into a plurality of device portion data files 1501-1 through 1501-X. In one embodiment, a processor, which may be processor 109 shown in FIG. 1 or another processor or processors, partitions each device data file 1301-1 through 1301-X into an anterior portion data file and a posterior portion data file corresponding respectively to an anterior portion and a posterior portion of a custom cranial remodeling orthosis device. In addition to partitioning each cranial remodeling orthosis device data file, processor 109, at step 1501, provides the subject identification information for each custom cranial remodeling device into the corresponding anterior and posterior portion data files.

Also, at step 1501, processor 109 or one or more other processors add portion identifying information into each anterior and posterior device portion data file to clearly identify the portion's location in assembly of the additive manufactured device portions into the corresponding custom cranial remodeling device. In this embodiment, there are only two device portions to each custom cranial remodeling orthosis device. In other embodiments there are more device portions and to remove any doubt as to where a device portion belongs in a custom cranial remodeling orthosis device, portion identifying information is helpful to insure proper assembly. It will be appreciated by those skilled in the art, that various identifiers may be used to identify a device portion's location, including, but not limited to, a symbolic identifier, an alphabetic identifier, and an alpha numeric identifier Still further processor 109 or one or more other processors may be programmed to provide, at step 1501, additional information for each cranial remodeling orthosis device into at least one device portion data file for each custom cranial remodeling device. That additional information may be traceable manufacturing information comprising one or more of date of manufacture, lot or batch number, machine identifier, a manufacture code, and other manufacture information for inclusion on at least one manufactured portion for a cranial remodeling orthosis device.

At step 1503, processor 109 or one or more other processors combines the partitioned device portion data files 1501-1 through 1501-X into a nested array data file. The arrangement of the nested array data file is such that the number or cranial remodeling orthosis devices and/or device portions that will be concurrently manufactured is maximized.

At step 1505, the nested array data file is processed by additive manufacture apparatus to concurrently manufacture a nested array of cranial remodeling orthosis device portions defined by the nested array data file.

Figure 16:
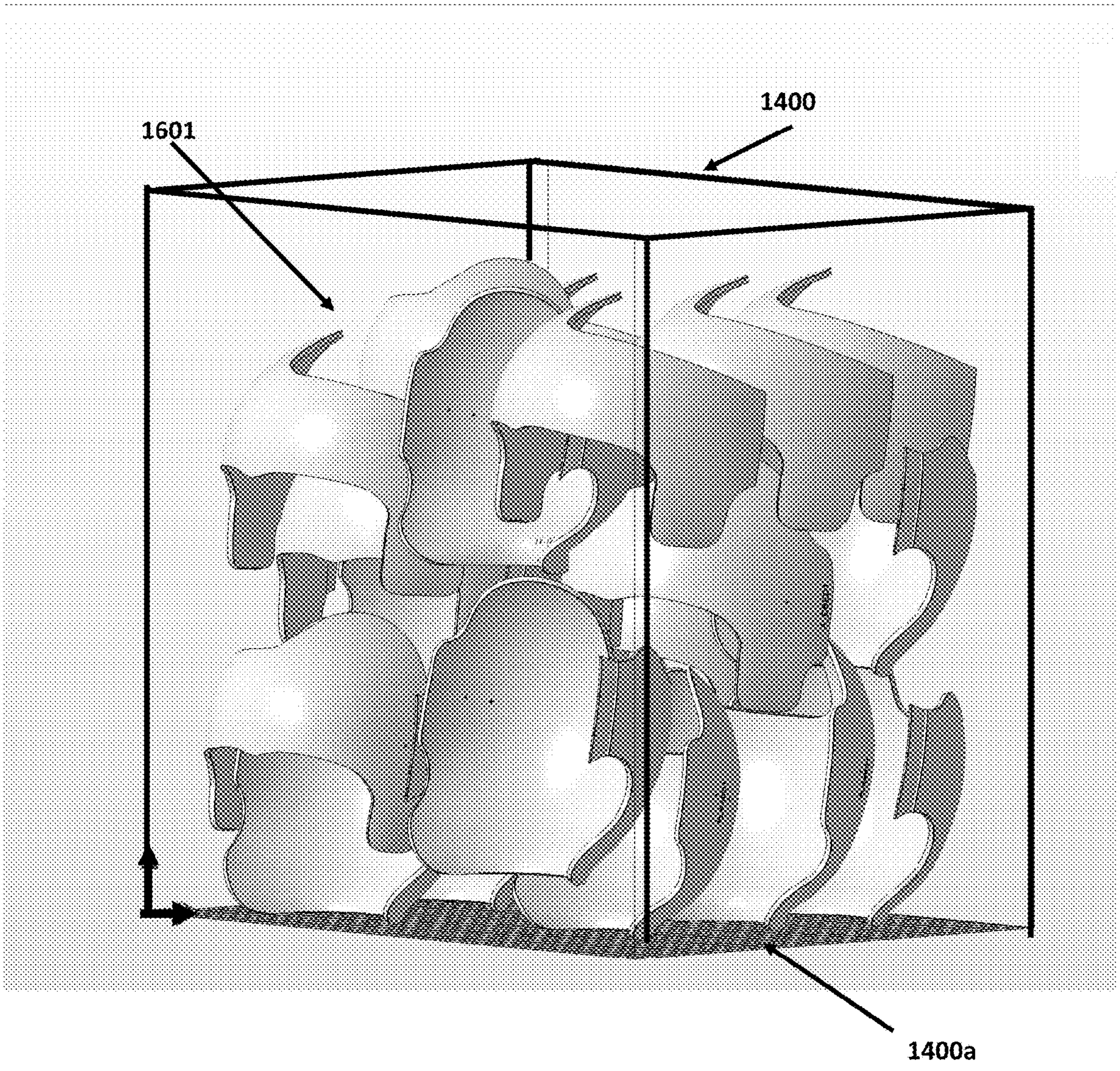
FIG. 16 is an isometric view of concurrent additive manufacture of partitioned cranial remodeling orthosis devices.

In FIG. 16 an exemplary nested array of cranial remodeling orthosis device portions 1601 is shown in chamber 1400.

Turning back to FIG. 15, the cranial remodeling orthosis device portions 1601 are assembled into the respective cranial remodeling orthosis devices at step 1507.

To assemble cranial remodeling orthosis device portions, integrally formed connecting portions are provided on each device portion. Processor 109 or one or more other processors that partition each device data file are further programmed to include connecting portion data corresponding to integrally formed connecting portions in each partitioned portion data file 1501-1 through 1501-Y at step 1501. Connecting portion data is such that when device portion data files are additively manufactured, corresponding integral connecting portions are formed on mating sides of cranial remodeling orthosis device portions to facilitate connectively assembling together adjacent cranial remodeling orthosis device portions. The connecting portions are not shown on the device portions in FIG. 16 for purposes of clarity, but are shown and described hereinafter.

Figure 17:
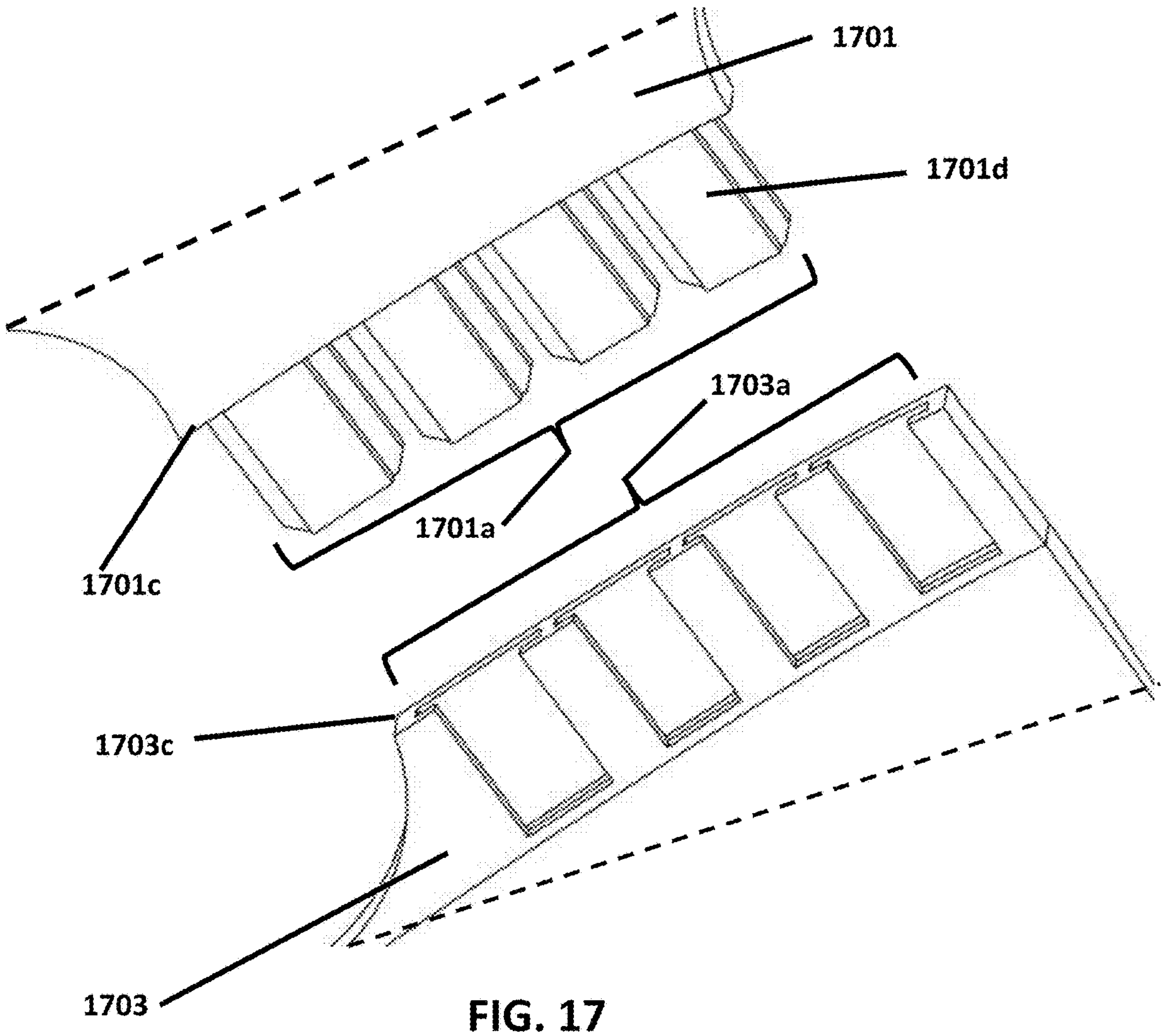
FIG. 17 illustrates portions of two cranial remodeling orthosis device portions as viewed from the interior of the cranial remodeling device.
Figure 18:
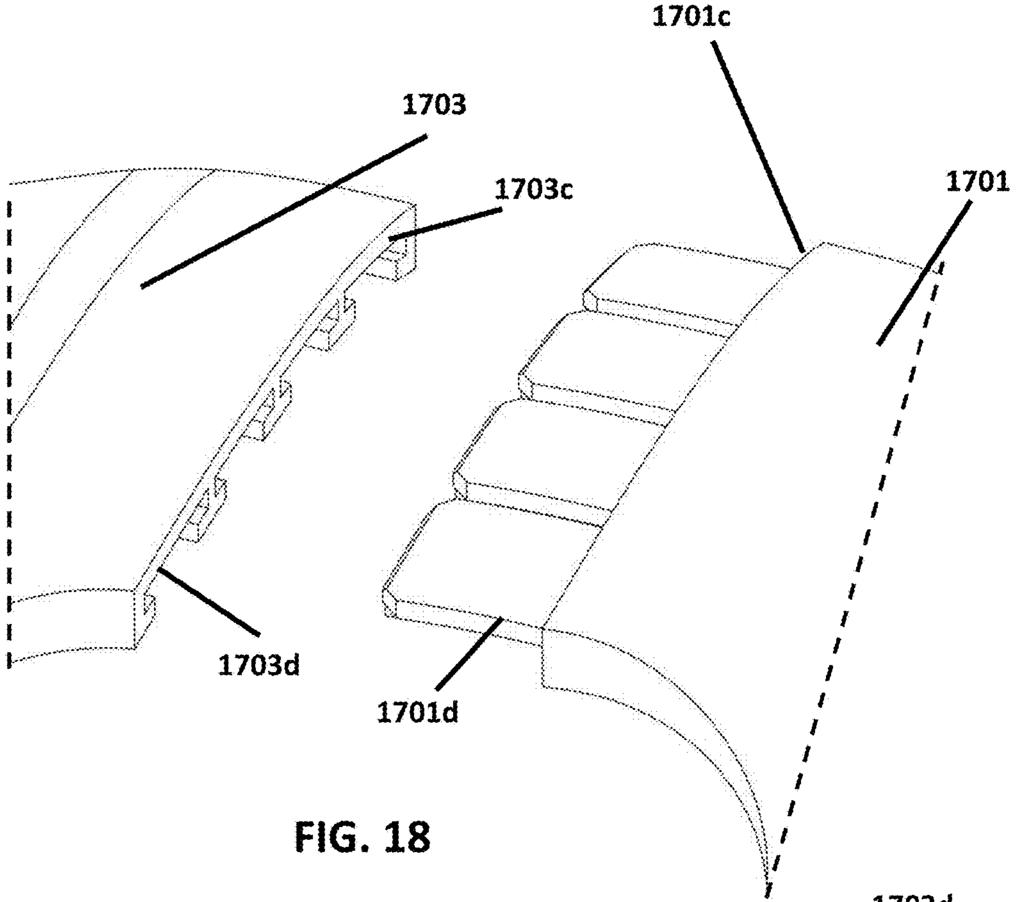
FIG. 18 illustrates the portions of two cranial remodeling orthosis device portions shown in FIG. 17 as viewed from the exterior of the cranial remodeling device.
Figure 20:
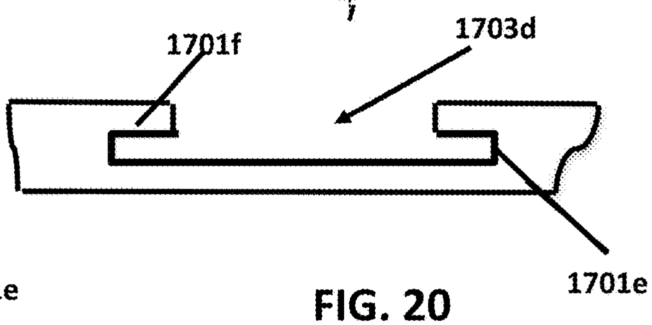
FIG. 20 is an end view of a corresponding connecting portion as viewed in the direction of arrow 1713 in FIG. 17.
Figure 19:
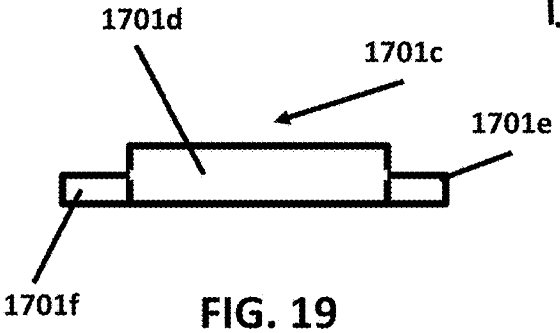
FIG. 19 is an end view of one connecting portion as viewed in the direction of arrow 1711 in FIG. 17.

FIGS. 17 and 18 illustrate exemplary connecting portions that may be integrally formed in cranial remodeling device portions to facilitate assembly. FIG. 17 illustrates two portions 1701, 1703 of a cranial remodeling orthosis device as viewed from the interior of the device and FIG. 18 illustrates the two portions 1701, 1703 of FIG. 17 from the outside of the cranial remodeling orthosis device. Cranial remodeling device portion 1701 carries a plurality of integrated connecting portions 1701*a* on its edge 1701*c* adjacent to device portion 1703 that carries corresponding integrated connecting portions 1703*a* on its edge 1703*c* adjacent to device portion 1701 edge 1701*c*. Connecting portions 1701*a* and 1701*c* are similar in function to tongue and groove connectors with connecting portions 1701*a* corresponding to tongues and connecting portions 1703*a* corresponding to grooves. Each tongue type portion 1701*a* includes side flanges 1701*e* and 1701*f* shown in an end view in FIG. 19 taken in the direction of arrow 1711 in FIG. 17. Side flanges 1701*e* and 1701*f* engage grooves 1703*e* and 1703*f* shown in and end view in FIG. 20 taken in the direction of arrow 1713 in FIG. 17. Each side flange 1701*e*, 1701*f* has its distal end beveled to facilitate insertion into grooves 1703*e* and 1703*f*.

In assembling the cranial remodeling orthosis device comprising device portions 1701 and 1703, connecting portions 1701*a* are slid into engagement with corresponding connecting portions 1703*a* such that cranial remodeling orthosis device portion edge 1701*c* is brought into contact with edge 1703*c*. By providing a plurality of connecting portions 1701*a* engaging a plurality of corresponding connecting portions 1703*a*, it has been found that the device portions 1701 and 1703 are securely engaged to each other.

The engagement of connecting portions 1701*a* and 1703*a* is such that device portions 1701 and 1703 are in locking engagement. In other embodiments, connecting portions 1701*a* and 1703*a* may be such that device portions may be removed and replaced.

Figure 21:
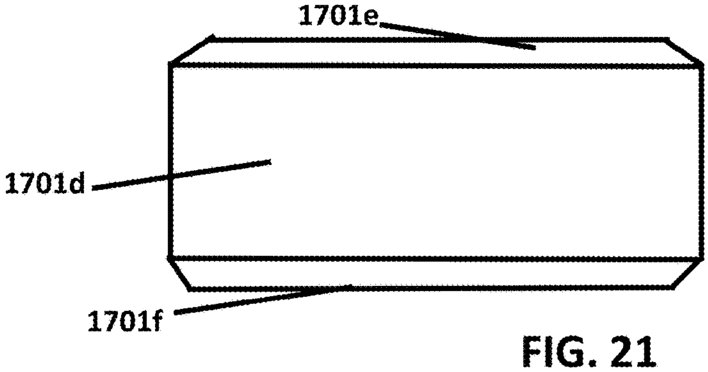
FIG. 21 is a top view of a connector.

In other embodiments, each cranial remodeling orthosis device portion may comprise integrally manufactured grooved portions 1703*a*. In these embodiments tongue type portions 1701*a* may comprise separately manufactured elongated portions or tongues 2001 shown in FIG. 21 that are inserted into connecting portions 1703*a*. In certain embodiments, tongues 2001 may lockingly engage connecting portions 1703*a* is such that device portions 1701 and 1703 are in locking engagement. In other certain embodiments, device portions may be removed and replaced.

Those skilled in the art will appreciate that although four connecting portions 1701*a* and four corresponding connecting portions 1703*a* are shown in FIGS. 17 and 18, that in other embodiments there may be more or less in number.

In addition, although tongue and groove connecting portion are show in FIGS. 17 through 20, other embodiments may utilize variations of the connecting members and corresponding connecting members or may utilize other types of mechanical connections. By way of non-limiting example, different types of tongue and groove type joints may be used to connect cranial remodeling orthosis device portions together, as well as lap type joints, snap fit type joints, finger type joints, locking type joints, click type joints, and dove tail type joints.

The invention is not limited to the illustrative connecting portions and corresponding connecting portions shown and described herein above. Other embodiments may utilize other fastening arrangements to couple together and retain cranial remodeling orthosis device portions into a cranial remodeling orthosis device.

In various embodiments, cranial remodeling orthosis device data files may be partitioned into an anterior portion data file and a posterior portion data file as described above. In other embodiments, device data files may be partitioned into an anterior portion data file and a plurality of posterior portion data files, a plurality of anterior portion data files and a plurality of posterior portion data files, a superior portion data file and an inferior portion data file, a superior portion data file and a plurality of inferior portion data files, a plurality of superior portion data files and a plurality of inferior portion data files or other combinations of device data file partitions. In certain embodiments, the selection of the partitions may be performed automatically by processor 109 or another processor or processors utilizing one or more algorithms to maximize the number of cranial remodeling orthosis devices and/or device portions that can be concurrently manufactured in portions in the particular sized production or build chamber being utilized. In certain other embodiments the partitioning may be predetermined.

In various embodiments, each device data file also includes date information that one or more algorithms may use to select the device data files to be partitioned and combined into a nested data array batch for concurrent manufacture to thereby assure that all custom cranial remodeling orthosis devices are timely manufactured.

Still further, in various embodiments each device data file may include priority information that is utilized by selection algorithms to prioritize manufacture of the corresponding custom cranial remodeling orthosis device.

Figure 22:
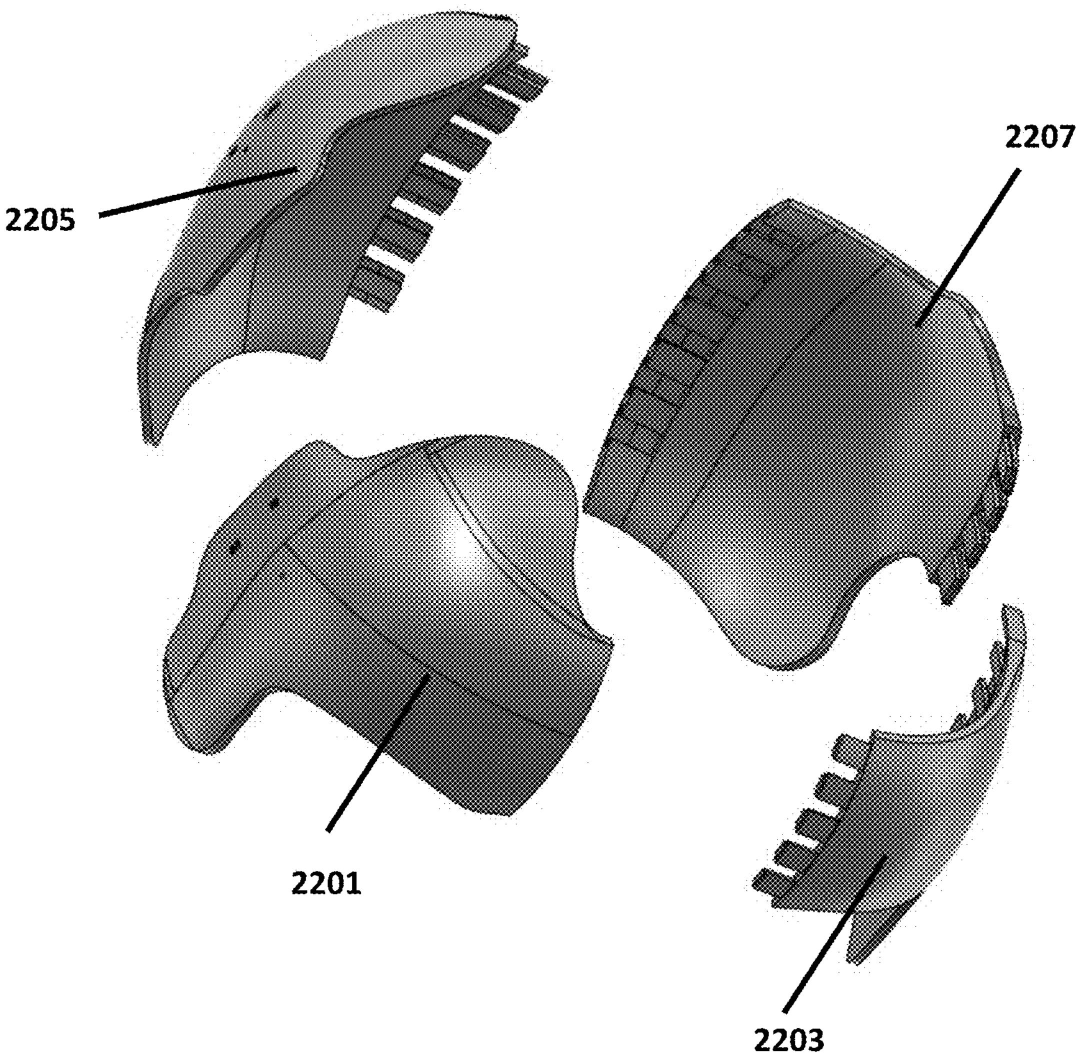
FIG. 22 is an isometric exploded view of a cranial remodeling orthosis device.

In one embodiment shown in FIG. 22, each cranial remodeling device is partitioned into four pieces, two anterior portions 2201, 2203 and two posterior portions 2205, 2207 using the methodology of FIG. 15 described above.

Figure 23:
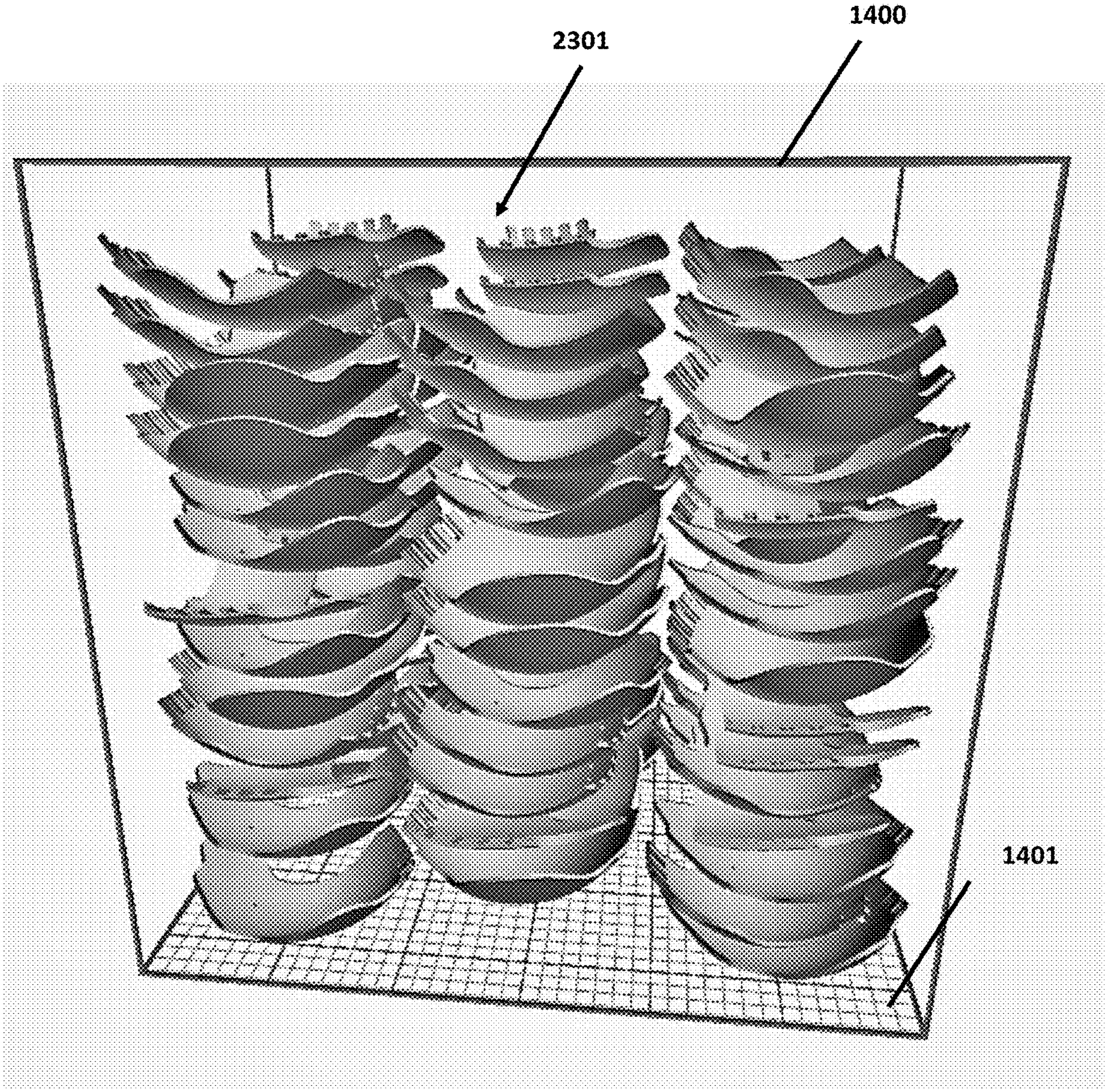
FIG. 23 is an isometric view of concurrent additive manufacture of partitioned cranial remodeling orthosis devices.
Figure 24:
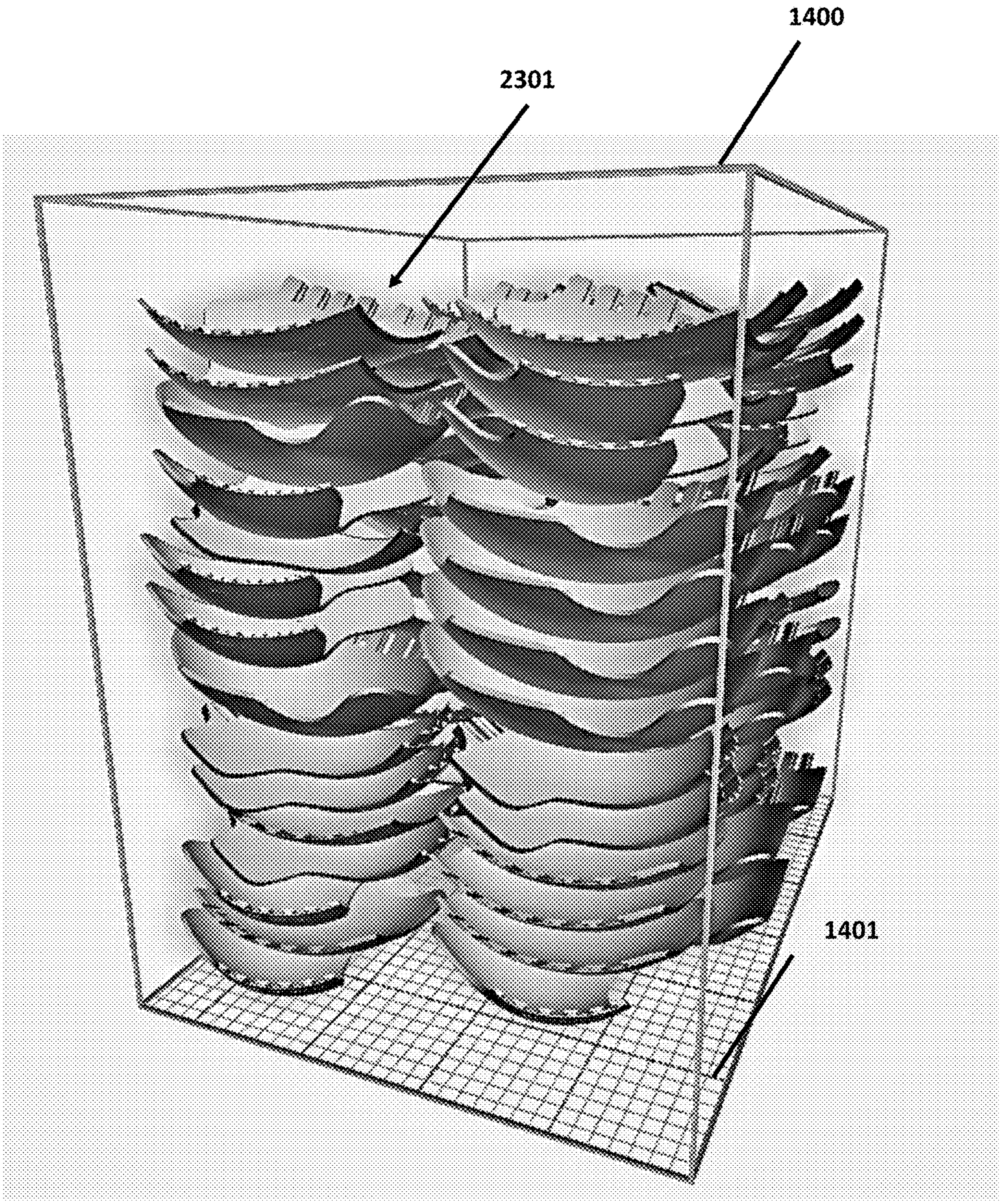
FIG. 24 is an isometric view of a production or build chamber shown in FIG. 23 from a different view.

By partitioning each cranial remodeling orthosis device data file into a first anterior portion data file, a second anterior portion data file, a first posterior data file and a second posterior data file a densely packed nested array data file is obtained corresponding to densely packed nested array 2301 of cranial remodeling orthosis device portions that are concurrently manufactured in a production or build chamber 1400 as shown in FIGS. 23 and 24.

In the embodiment shown in FIGS. 23 and 24, eighty (80) device portions 2301 are concurrently manufactured for assembly into 20 cranial remodeling orthosis devices. The manufacturing throughput and time efficiency is greatly increased by concurrent manufacture of partitioned cranial remodeling orthosis device data files.

Variations of the embodiment of methods in which a plurality of entire cranial remodeling orthosis devices is concurrently manufactured that have been developed are described below.

A method of manufacturing a plurality of cranial remodeling orthosis devices may comprise receiving a plurality of device data files, each corresponding to a custom cranial remodeling orthosis device and generating a nested array device data file from the plurality of device data files. The nested array device data file is arranged for concurrent manufacture by additive manufacture apparatus.

The method may comprise utilizing predetermined selection criteria to select ones of said plurality of device data files for inclusion into the nested array device data file.

The predetermined selection criteria may comprise one of more of age of patient, location of patient, date of formation of a device file, date of receipt of a device file, geographic location where a cranial remodeling orthosis device is received from or to be sent, size of a cranial remodeling device, type of cranial remodeling device.

The method may comprise utilizing one or more first algorithms to select and arrange the device data files into the nested array data file.

The nested array device data file may be arranged to maximize the number of cranial remodeling orthosis devices to be concurrently manufactured.

The method may comprise utilizing one or more algorithms to select the plurality of device files from a first plurality of device data files. The plurality of device data files may be selected by one or more first algorithms utilizing predetermined selection criteria.

The predetermined selection criteria may comprise one of more of age of patient, location of patient, date of formation of a device file, date of receipt of a device file, geographic location where a cranial remodeling orthosis device is received from or to be sent, size of a cranial remodeling device, type of cranial remodeling device.

The method may comprise utilizing the nested array device data file to concurrently manufacture a plurality of cranial remodeling orthosis devices in an additive manufacture production chamber.

The method may comprise utilizing one or more algorithms to select the plurality of device files from a first plurality of device data files. The plurality of device data files may be selected by one or more first algorithms utilizing predetermined selection criteria.

A further method of manufacturing a plurality of cranial remodeling orthosis devices comprises receiving a first plurality of device data files, each corresponding to a custom cranial remodeling orthosis device and utilizing one or more algorithms to select a plurality of device data files from the first plurality of device data files. The plurality of device data files may be selected by one or more first algorithms utilizing predetermined selection criteria. The method further comprises combining the plurality of device data files into a nested array device data file.

The further method may comprise utilizing predetermined selection criteria to select the plurality of device data files.

In the further method, the predetermined selection criteria may comprise one of more of age of patient, date of formation of a device file, date of receipt of a device file, geographic location where a cranial remodeling orthosis device is to be sent, type of cranial remodeling orthosis device, and size of a cranial remodeling orthosis device.

The further method may comprise selecting the size of the nested array device data file to fit within a production chamber of an additive manufacture apparatus.

The further method may comprise utilizing the nested array device data file to concurrently manufacture a corresponding plurality of custom cranial remodeling devices with the additive manufacture apparatus.

The further method may comprise utilizing predetermined selection criteria to select the plurality of device data files.

In the further method, the predetermined selection criteria may comprise one or more of age of patient, date of formation of a device file, date of receipt of a device file, geographic location where a cranial remodeling orthosis device is to be sent, type of cranial remodeling orthosis device, and size of a cranial remodeling orthosis device.

In the further method, the nested array device data file may be used to concurrently manufacture a corresponding plurality of custom cranial remodeling devices with additive manufacture apparatus.

The further method may comprise utilizing the nested array device data file to concurrently manufacture a corresponding plurality of custom cranial remodeling devices with fusion bed additive manufacture apparatus.

Variations of the embodiments of the methods in which cranial remodeling orthosis device data files are partitioned to concurrently manufacture a plurality of entire cranial remodeling orthosis devices are described below.

A first method of manufacturing a custom cranial remodeling device for a corresponding subject, wherein the cranial remodeling device is represented by a device data file, comprises partitioning the device data file into a plurality of device portion data files, each device portion data file corresponding to a device portion of the cranial remodeling device; and processing the plurality of device portion data files to provide a data file array comprising an array of the plurality of device portion data files for manufacture by additive manufacturing apparatus. The array of the device portion data files comprises one of a corresponding planar array, a nested array and a combination planar and nested array of a plurality of device portions of the cranial remodeling device. The method further comprises processing the data file array for concurrently manufacturing the plurality of device portions by additive manufacture apparatus.

The method of the first embodiment may comprise assembling the plurality of device portions together to form the cranial remodeling device.

The first embodiment method may further comprise providing each device portion data file with data corresponding to one or more integrally formed connecting portions to engage with one or more corresponding connecting portions carried by one or more adjacent other device portions when the plurality of device portions is manufactured and assembled together to unitarily form the cranial remodeling device.

The first embodiment method may further comprise arranging each connecting portion carried by a device portion to securely affix the device portion with a corresponding connection portion carried by an adjacent device portion when the device portions are assembled together.

The first method may further comprise partitioning the corresponding device data file into at least one anterior cranial remodeling device portion and at least one posterior cranial remodeling device portion.

The first embodiment method may further comprise partitioning the corresponding device data file into a plurality of anterior cranial remodeling device portion and at least one posterior cranial remodeling device portion.

The first embodiment method may comprise partitioning the corresponding device data file into at least one anterior cranial remodeling device portion and a plurality of posterior cranial remodeling device portions.

The first embodiment method may comprise partitioning the corresponding device data file into a plurality of anterior device cranial remodeling device portions and a plurality of posterior cranial remodeling device portions.

The first embodiment method may comprise processing each of the plurality of device portion data files to include identification information for each device portion. The identification information for each said device portion indicating a position of said device portion in said cranial remodeling device. The method further comprises processing the data file array to integrally manufacture the identification information onto each device portion.

The first embodiment method may comprise processing each of the plurality of device portion data files to include subject identification information for each device portion, and processing the data file array to integrally manufacture subject identification information onto each device portion.

The first embodiment method may comprise processing each of the plurality of device portion data files to include on at least one device portion for a cranial remodeling orthosis device manufacturing identification information, and processing the data file array to provide integrally manufactured identification information onto each device portion.

The first embodiment method may comprise processing each device portion data files to include assembly alignment marks, and processing the data file array to integrally manufacture the assembly alignment marks onto each device portion. The alignment marks may be any one of a number of types of marks on each mating portion of a cranial remodeling orthosis device to assure that the device portions are in mating alignment when the device portions are assembled together. One, non-limiting example of such marks includes a semicircle on each portion positioned so that when adjacent portions are in correct assembled alignment a full circle is shown. Other types of alignment marks may be utilized and the invention is not limited to the use of any particular types of alignment marks. Alignment marks may be carried on the inner surface or the outer surface of the assembled cranial remodeling orthosis device.

The first embodiment method may comprise combining a device data file portion array with one or more other device data file portion arrays for one or more corresponding other subject cranial remodeling orthosis devices to provide a nested array for concurrent manufacture of a plurality of cranial remodeling orthosis device portions.

The first embodiment method may comprise processing the device data file in accordance with one or more algorithms to determine partitioning of the device data file into cranial remodeling orthosis device portion data files.

The first embodiment method may comprise processing the plurality of device portion data files to determine placement of integrally formed connecting portions and corresponding connecting portions carried by the plurality of device portions to facilitate assembly of said plurality of device portions into a cranial remodeling orthosis device.

The first embodiment method may comprise processing device portion data files to determine numbers and placements of integrally formed connecting portions and corresponding connecting portions carried by the plurality of device portions to facilitate assembly into a cranial remodeling orthosis device.

The first embodiment method may comprise processing the device data file to determine a number and position of the plurality of device data files for a cranial remodeling device.

The first embodiment method may comprise processing the plurality of device portion data files to arrange the data file array for efficient manufacture of said plurality of device portions by additive manufacture.

The first embodiment method may comprise manufacturing the plurality of device portions by additive manufacture.

The first embodiment method may comprise manufacturing the plurality of device portions by utilizing powder bed fusion additive manufacture.

Another embodiment of a method of concurrent additive manufacture of a plurality of custom cranial remodeling orthosis devices for a corresponding plurality of subjects is provided wherein each cranial remodeling orthosis device is customized for a different one subject of said plurality of subjects, and in which each cranial remodeling orthosis device is represented by a corresponding device data file of a plurality of device data files. The method comprises partitioning each corresponding device data file into a plurality of device portion data files, each device portion data file corresponding to a device portion of a corresponding cranial remodeling orthosis device. The method further comprises processing each device portion data file into a nested data file array corresponding to a nested device portions array comprising each said device portion of each said cranial remodeling orthosis device of the plurality of cranial remodeling orthosis devices.

The another embodiment of a method of concurrent additive manufacture of a plurality of custom cranial remodeling devices may comprise processing the nested data array to concurrently manufacture the nested portions array by additive manufacture.

The another embodiment of a method of concurrent additive manufacture of a plurality of custom cranial remodeling devices may comprise assembling the device portions from the manufactured nested portions array into the plurality of cranial remodeling devices.

The another embodiment of a method of concurrent additive manufacture of a plurality of custom cranial remodeling devices may comprise processing the plurality of device portion data files for each cranial remodeling device to include subject identification data, all of device portion files for a corresponding cranial remodeling device comprising the same subject identification data.

The another embodiment of a method of concurrent additive manufacture of a plurality of custom cranial remodeling devices may comprise processing nested data arrays to concurrently manufacture corresponding nested portions arrays by additive manufacture, each manufactured device portion carrying corresponding subject identification data.

The another embodiment of a method of concurrent additive manufacture of a plurality of custom cranial remodeling devices may comprise assembling each cranial remodeling device from device portions carrying same subject identification data.

The another embodiment of a method of concurrent additive manufacture of a plurality of custom cranial remodeling devices may comprise processing the plurality of device portion data files for each corresponding cranial remodeling device to include part identification data. The part identification data is included on each manufactured device portion of the corresponding cranial remodeling device.

The another embodiment of a method of concurrent additive manufacture of a plurality of custom cranial remodeling devices may further include processing the plurality of device portion data files for each cranial remodeling device to include subject identification data included on each manufactured device portion. The subject identification data is the same for all manufactured device portions for the corresponding cranial remodeling device.

The another embodiment of a method of concurrent additive manufacture of a plurality of custom cranial remodeling devices may additionally include processing the data array by additive manufacture apparatus to concurrently manufacture the device portions. Each manufactured device portion carries corresponding subject identification information and corresponding device part information.

The another embodiment of a method of concurrent additive manufacture of a plurality of custom cranial remodeling devices may comprise processing the plurality of device portion data files for each corresponding cranial remodeling device to include integral connecting portions to interconnect each manufactured device portion with one or more adjacent manufactured device portions of the corresponding cranial remodeling device.

The embodiment of a method of concurrent additive manufacture of a plurality of custom cranial remodeling devices may comprise processing the data array by additive manufacture apparatus to concurrently manufacture the device portions.

The another embodiment of a method of concurrent additive manufacture of a plurality of custom cranial remodeling devices may comprise assembling together device portions for each corresponding cranial remodeling device by utilizing the connecting portions to affix each of the device portions to its adjacent one or more device portions.

The another embodiment of a method of concurrent additive manufacture of a plurality of custom cranial remodeling devices may comprise providing each device portion data file of the plurality of device portion data files for a corresponding cranial remodeling device with data for one or more integrally formed connecting portions to be coupled with one or more corresponding connecting portions carried by one or more adjacent other device portions of the corresponding cranial remodeling device after the plurality of portions are manufactured.

The another embodiment of a method of concurrent additive manufacture of a plurality of custom cranial remodeling devices may comprise processing the data array by additive manufacture apparatus to concurrently manufacture the device portions.

The another embodiment of a method of concurrent additive manufacture of a plurality of custom cranial remodeling devices may comprise assembling together device portions for each corresponding cranial remodeling device by utilizing connecting portions to affix each of the device portions to its adjacent one or more device portions.

The another embodiment of a method of concurrent additive manufacture of a plurality of custom cranial remodeling devices may comprise processing the plurality of device portion data files to determine quantities and locations of connecting portions for each of the device portions.

The another embodiment of a method of concurrent additive manufacture of a plurality of custom cranial remodeling devices may comprise partitioning each corresponding device data file into at least one anterior device portion data file corresponding to an anterior device portion of a corresponding cranial remodeling device and at least one posterior device portion data file corresponding to a posterior device portion of a corresponding cranial remodeling device.

The another embodiment of a method of concurrent additive manufacture of a plurality of custom cranial remodeling devices may comprise processing the data array by additive manufacture apparatus to concurrently manufacture the at least one anterior device portion and the at least one posterior device portion of the cranial remodeling devices.

The another embodiment of a method of concurrent additive manufacture of a plurality of custom cranial remodeling devices may comprise partitioning each corresponding device data file into at least one anterior device portion data file corresponding to an anterior device portion of a corresponding cranial remodeling device and a plurality of posterior device portion data files each corresponding to a device posterior device portion of a corresponding cranial remodeling device.

The another embodiment of a method of concurrent additive manufacture of a plurality of custom cranial remodeling devices may comprise processing the data array by additive manufacture apparatus to concurrently manufacture at least one anterior device portion and the plurality of posterior device portions of the cranial remodeling devices.

Variations of the embodiment of a cranial remodeling orthosis device manufacturable by additive manufacturing apparatus that have been developed are described below.

One embodiment of a cranial remodeling orthosis, comprises an anterior portion and a posterior portion comprising a plurality of posterior device portions. The plurality of posterior device portions are affixed together to form a continuous, uninterrupted unitary posterior portion. The unitary posterior portion is affixed to the anterior portion to form a continuous, uninterrupted, and unitary cranial remodeling orthosis.

Each of the plurality of posterior device portions comprises integral connecting portions. The plurality of posterior device portions are assembled together utilizing corresponding integral connecting portions to form the continuous, uninterrupted, unitary posterior portion.

The anterior portions also comprise integral connecting portions. The anterior portion and the unitary posterior portion are affixed together utilizing corresponding connecting portions on the anterior portion and the unitary posterior portion to form a continuous, uninterrupted, unitary cranial remodeling orthosis.

Each of the connecting portions may comprise one of a tongue and groove type joint, a lap type joint, one or more snap fit joints, one or more finger joints, a locking type joint, a click type joint, and a dovetail type joint.

In the embodiment the anterior portion may comprise a plurality of anterior device portions. The plurality of anterior device portions are affixed together to form a continuous, uninterrupted, unitary anterior portion.

In the embodiment, the plurality of anterior device portions may be assembled together with integral formed connecting portions and the plurality of anterior device portions are assembled together with the posterior portion to form a continuous, uninterrupted unitary cranial remodeling orthosis.

In the embodiment, each of the plurality of posterior device portions and each of the plurality of anterior device portions is manufactured by additive manufacture.

The embodiment may comprise a first peripheral edge on an inner surface, a second peripheral edge on an outer surface and a beveled surface between the first peripheral edge and the second peripheral edge.

A second embodiment of a custom manufactured cranial remodeling orthosis comprises an anterior portion and a posterior portion. The anterior portion comprises one or more additive manufactured anterior device portions. The posterior portion comprises a plurality of additive manufactured posterior device portions. The one or more anterior device portions and the plurality of posterior device portions are assembled together to form a continuous, uninterrupted, unitary custom manufactured cranial remodeling orthosis.

The second embodiment may comprise connecting portions integrally formed on said one or more anterior device portions and on said plurality of posterior device portions. The connecting portions affix adjacent one or more anterior portions and the plurality of posterior portions together to form said continuous, uninterrupted, unitary custom manufactured cranial remodeling orthosis.

The embodiments may comprise a first peripheral edge on an inner surface, a second peripheral edge on an outer surface and a beveled surface between the first peripheral edge and the second peripheral edge.

A third embodiment of a custom manufactured cranial remodeling device for modifying the shape of a subject's head comprises a plurality of device portions manufactured by additive manufacture. Each of the device portions comprises one or more integral connecting portions. The device portions are interconnected together utilizing the one or more corresponding connecting portions to form a continuous, uninterrupted, unitary cranial remodeling device.

The third embodiment may comprise at least one anterior device portion and at least one posterior device portion. The at least one anterior device portion is affixed to the at least one posterior device portion utilizing the connecting portions and corresponding connecting portions.

The third embodiment may comprise one anterior device portion and a plurality of posterior device portions. The posterior portions are affixed to each other utilizing the connecting portions and the corresponding connecting portions to form a unitary posterior portion. The unitary posterior portion is affixed to the one anterior portion utilizing connecting portions and corresponding connecting portions.

In the third embodiment, the connecting portions are configured to provide locking connections between adjacent device portions.

In the third embodiment, the connecting portions may comprise one of tongue and groove type joints, lap type joints, one or more snap fit type joints, one or more finger type joints, locking type joints, click type joints, and dove tail type joint.

In the third embodiment the plurality of device portions may comprise one of: an anterior portion and a plurality of posterior portions, a plurality of anterior portions and a plurality of posterior portions, a plurality of anterior portions and a posterior portion, a superior portion and an inferior portion, a plurality of superior portions and a plurality of inferior portions, a superior portion and a plurality of inferior portions, and a plurality of superior portions and an inferior portion.

The third embodiment may comprise a first superior peripheral edge on an inner surface, a second superior peripheral edge on an outer surface, and a superior beveled surface between the first superior peripheral edge and the second superior peripheral edge. In addition, the third embodiment may comprise a first inferior peripheral edge on an inner surface, a second inferior peripheral edge on an outer surface, and an inferior beveled surface between the first superior peripheral edge and the second superior peripheral edge.

A fourth embodiment of a cranial remodeling orthosis, comprises a separate superior portion and a separate inferior portion. The separate superior portion affixed to the separate inferior portion to form the cranial remodeling orthosis.

In the fourth embodiment each of the separate superior portion and the separate inferior portion may comprise one or more integral connecting portions. The separate superior portion and separate inferior portions are assembled together to form a continuous, uninterrupted, unitary cranial remodeling orthosis.

In the fourth embodiment the inferior portion may comprise a plurality of inferior sub-portions. Each of the inferior sub-portions comprises one or more integral connecting portions. The inferior sub-portions are affixed together utilizing corresponding connecting portions on the inferior sub-portions.

In the fourth embodiment, the separate superior portion may comprise one or more superior sub-portions. The separate inferior portion comprises one or more inferior sub-portions. Each of the one or more superior sub-portions and each of the one or more inferior sub-portions comprises one or more connecting portions. The one or more superior sub-portions and the one or more inferior sub-portions are assembled together in a continuous, uninterrupted, unitary cranial remodeling orthosis.

In the fourth embodiment, each of the connecting portions may comprise one of a tongue and groove type joint, a lap type joint, one or more snap fit joints, one or more finger joints, a locking type joint, a click type joint, and a dovetail type joint.

The fourth embodiment comprises an inner surface configured to remodel the head of a subject when the cranial remodeling orthosis is worn by a subject with a deformed head shape, and an outer surface.

In the fourth embodiment, the separate superior portion comprises a superior inner peripheral edge at the inner surface and a superior outer peripheral edge at the outer surface. The separate inferior portion comprises an inferior inner peripheral edge at the inner surface and an inferior outer peripheral edge at the outer surface.

In the fourth embodiment, the inferior inner peripheral edge is determined from one or more of anthropometric points, curvatures or features on the deformed head shape.

The fourth embodiment may comprise an inferior peripheral surface extending between the inferior inner peripheral edge and the inferior outer peripheral edge. The inferior outer peripheral edge is offset from the inferior inner peripheral edge by a predetermined offset.

In the fourth embodiment, each of said one or more superior sub-portions and each of said one or more inferior sub-portions is manufactured by additive manufacture.

A fifth embodiment of a cranial remodeling orthosis manufactured by additive manufacture, comprises a plurality of separate additive manufactured portions. Each of the separate additive manufactured portions comprises one or more integrally formed connecting portions. Each connecting portion is utilized to engage a corresponding connecting portion on an adjacent separate additive manufactured portion to affix the plurality of separate additive manufactured portions into the cranial remodeling orthosis.

In the fifth embodiment, the plurality of separate additive manufactured portions may comprise one or more superior portions and one or more inferior portions.

In the fifth embodiment, the one or more superior portions may comprise one or more anterior superior portions and one or more posterior superior portions. The one or more inferior portions comprise one or more anterior inferior portions and one or more posterior inferior portions.

In the fifth embodiment, the plurality of separate additive manufactured portions may comprise one or more anterior portions and one or more posterior portions.

In the fifth embodiment, the one or more anterior portions may comprise one or more superior anterior portions and one or more inferior anterior portions. The one or more posterior portions may comprise one or more superior posterior portions and one or more inferior posterior portions.

In the fifth embodiment, the integrally formed connecting portions may each comprise one of tongue and groove type joints, lap type joints, one or more snap fit type joints, one or more finger type joints, locking type joints, click type joints, and dove tail type joint.

In the fifth embodiment, the plurality of separate additive manufactured portions may be determined by an algorithm processing a cranial remodeling orthosis device data file to partition said device data file into a corresponding plurality of data file portions.

In the fifth embodiment, the plurality of separate additive manufactured portions may comprise one or more superior portions and one or more inferior portions.

In the fifth embodiment, the plurality of separate additive manufactured portions may comprise one or more anterior portions and one or more posterior portions.

In the fifth embodiment, the number and placement of each of the integrally formed connecting portions are determined by an algorithm.

A sixth embodiment of a custom cranial remodeling orthosis to modify the shape of a deformed head of a subject comprises an inner layer carrying an inner surface shaped to provide modification of the shape of the deformed head. The inner surface comprises an inner surface peripheral edge. The sixth embodiment further comprises an outer layer carrying an outer surface, the outer surface comprises an outer surface peripheral edge. The inner surface and the outer surface each comprise a shape determined from a device data file representative of the shape of the cranial remodeling orthosis. At least one of the inner surface peripheral edge and the outer surface peripheral edge is determined from one or more of curvatures, features, and reference points on the shape of the deformed head. The inner surface peripheral edge and the outer surface peripheral edge are offset from each other.

The sixth embodiment may comprise a peripheral surface between the inner surface peripheral edge and the outer surface peripheral edge.

In the sixth embodiment, the peripheral surface is beveled from the inner surface peripheral edge to the outer surface peripheral edge.

In the sixth embodiment, the inner surface peripheral edge may be determined from one or more of curvatures, features, and reference points on said shape of the deformed head represented by a subject data file.

In the sixth embodiment, the offset is uniform along the entirety of the inner surface peripheral edge and the outer surface peripheral edge.

In the sixth embodiment, the inner surface peripheral edge is carried on an inferior portion of the cranial remodeling orthosis, and the outer surface peripheral edge is carried on the inferior portion of the cranial remodeling orthosis.

The sixth embodiment may comprise an inner surface superior peripheral edge carried on a superior portion of the cranial remodeling orthosis, and an outer surface superior peripheral edge carried on the superior portion of the cranial remodeling orthosis.

The sixth embodiment may comprise a superior peripheral surface between the inner surface superior peripheral edge and the outer surface superior peripheral edge.

In the sixth embodiment, the superior peripheral surface may be beveled from the inner surface superior peripheral edge to the outer surface superior peripheral edge.

In the sixth embodiment, the inner surface superior peripheral edge may be determined from one or more of curvatures, features, and reference points on the shape of the deformed head represented by a subject data file.

In the sixth embodiment, the offset may be uniform along the entirety of the inner surface superior peripheral edge and the outer surface superior peripheral edge.

A seventh embodiment of a custom cranial remodeling orthosis to modify the shape of a deformed head of a subject comprises an inner layer carrying an inner surface shaped to provide modification of the shape of the deformed head. The inner layer comprises material deposited by additive manufacture. The embodiment further comprises an outer layer carrying an outer surface. The outer layer comprises material deposited by additive manufacture. The inner surface and the outer surface each have a shape determined from a device data file representative of the shape of the cranial remodeling orthosis. The inner surface comprises an inferior inner peripheral edge. The outer surface comprises an inferior outer peripheral edge. The inner surface inferior inner peripheral edge is determined from one or more of curvatures, features, and anthropometric reference points on said shape of said deformed head.

In the seventh embodiment, the inferior outer peripheral edge may be offset from said inner peripheral edge.

The seventh embodiment may comprise an inferior peripheral surface between the inferior inner peripheral edge and the inferior outer peripheral edge.

In the seventh embodiment, the inner surface may comprise a superior inner peripheral edge, the outer surface may comprise a superior outer peripheral edge, and the inner surface superior inner peripheral edge may be determined from one or more of curvatures, features, and reference points on the shape of the deformed head.

In the seventh amendment, the superior outer peripheral edge may be offset from the superior inner peripheral edge.

The seventh embodiment may comprise a superior peripheral surface between the superior inner peripheral edge and the superior outer peripheral edge and the inferior outer peripheral edge may be offset from the inner peripheral edge.

In the seventh embodiment, the inferior inner peripheral edge may be determined from one or more of curvatures, features, and reference points on the shape of the deformed head represented by a subject data file, and the superior inner peripheral edge may be determined from one or more of curvatures, features, and reference points on the shape of the deformed head represented by a subject data file.

The various embodiments described with respect to cranial remodeling orthosis devices may be utilized with respect to other types of headwear.

Various connecting arrangements for affixing cranial remodeling orthosis devices are provided.

One embodiment of a cranial remodeling orthosis device for modifying the shape of a subject's head, comprises a plurality of device portions manufactured with additive manufacture material. Each of the device portions comprises one or more of first and second connecting portions. Each first connecting portion comprises an elongate member and each second connecting portion is configured to receive and retain one elongate member. The plurality of device portions is interconnected together utilizing the one or more first and second connecting portions such that each device portion is fastened to one or more adjacent device portions.

In the one embodiment, the first connecting portion may be integrally formed with its respective device portion and each second connecting portion is integrally formed with its respective device portion.

In the one embodiment, each second connecting portion is integral to its corresponding device portion and may comprise a channel configured to receive a corresponding elongate member.

In the one embodiment each second connecting portion may comprise a channel disposed in a surface of its corresponding device portion with the channel being configured to receive and retain one corresponding elongate member.

In the one embodiment, each elongate member may comprise first and second lateral flanges and the channel comprises lateral channels to receive the first and second lateral flanges In the one embodiment, each elongate member may comprise a longitudinal portion extending from the corresponding device portion, and the longitudinal portion carries one or more lateral flanges extending transversely from the longitudinal portion. In addition, each second connecting portion comprises a longitudinal channel configured to receive the longitudinal portion and one or more lateral channels transverse to the longitudinal channel to receive the one or more lateral flanges carried by a corresponding elongate member.

In the one embodiment, each device portion is additively manufactured and each first connecting portion and each second connecting portion is integrally formed on its respective device portion.

In another embodiment, the first device portion manufactured with additive manufacture material may comprise a plurality of first integrally formed connecting portions each disposed along a first edge of the first device portion, and the second device portion manufactured with additive manufacture material may comprise a plurality of second integrally formed connecting portions each disposed along a first edge of the second device portion. The first and second device portions are assembled together along the first device portion first edge and the second device portion first edge utilizing the first and second integrally formed connecting portions.

In the another embodiment, each first connecting portion may comprise a longitudinal member extending from the first edge of the first portion, and each second connecting portion may comprise a channel configured to receive and retain a corresponding longitudinal member.

In the another embodiment each longitudinal member may comprise transverse flanges extending from the longitudinal member, and each second connecting portion may comprise channels configured to engage the transverse flanges.

The another embodiment may comprise a plurality of elongate members, each configured to engage one of the first connecting portions and a corresponding one of the second connecting portions.

In the another embodiment each elongate member may comprises transversely extending flanges, and each first and second connecting member may comprise channels configured to engage the flanges to retain the first device portion first edge in engagement with the second device portion first edge.

A further embodiment may comprise a plurality of device portions manufactured with additive manufacture material with adjacent ones of the device portions connected together edge to edge. Each device portion may comprise a plurality of integrally formed connecting portions each disposed along each edge adjacent to another one of the device portions. Each of the plurality of integrally formed connecting portions on one device portion is in engaging connection with a corresponding plurality of integrally formed connection portions on an adjacent one of the device portions to retain the adjacent portions together.

In the further embodiment, predetermined ones of the plurality of connecting portions each carry an elongate connecting member, and predetermined other ones of the plurality of connecting portions each comprise a channel for receiving and retaining a corresponding elongate connecting member.

In the further embodiment, each elongate connecting member may be integrally formed with its corresponding device portion.

In the further embodiment each elongate member may comprise transverse flanges, and each channel comprises transverse channels to engage said transverse flanges.

The further embodiment may comprise a plurality of elongate members, and each of the integrally formed connecting portions may comprise a channel receiving a corresponding one of said elongate members.

In the further embodiment, each elongate member may comprise transverse flanges, and each channel may comprise transverse channels to engage transverse flanges.

The invention has been described in terms of various embodiments. It will be apparent to those skilled in the art that various modifications may be made without departing from the scope of the invention. There is no intention to limit the invention to the embodiments shown. It is intended that the invention be limited in scope only by the claims appended hereto.

The invention claimed is:

1. A custom manufactured cranial remodeling orthosis device for modifying a shape of a particular subject's head, comprising: at least three device portions manufactured with additive manufacture material; each device portion of said at least three device portions comprising a continuous, monolithic outer surface over said each device portion outer surface entirety and a continuous, monolithic inner surface over said each device portion inner surface entirety; each device portion of said at least three device portions comprising one or more integral connecting portions disposed between said continuous, monolithic outer surface and said continuous, monolithic inner surface; said one or more integral connecting portions of each device portion of said at least three device portions configured to lockingly engage corresponding one or more integral connecting portions of an adjacent one device portion of said at least three device portions; said at least three device portions interconnected together utilizing said one or more integral connecting portions to form a unitary cranial remodeling orthosis device.

2. The custom manufactured cranial remodeling orthosis device of claim 1, comprising: said at least three device portions comprising one or more anterior device portions and a plurality of posterior device portions; said plurality of posterior portions affixed to each other each utilizing a plurality of integral connecting portions to form a monolithic posterior portion; and said monolithic posterior portion affixed to said one or more anterior device portions utilizing one or more integral connecting portions.

3. The custom manufactured cranial remodeling orthosis device of claim 2, wherein: said one or more integral connecting portions are configured to provide locking connections between adjacent posterior device portions of said plurality of posterior portions and said one or more anterior device portions.

4. The custom manufactured cranial remodeling orthosis device of claim 1, comprising: said at least three device portions comprising at least one anterior device portion and at least one posterior device portion; said at least one anterior device portion affixed to said at least one posterior device portion with said one or more integral connecting portions to form a monolithic cranial remodeling orthosis device.

5. The custom manufactured cranial remodeling orthosis device of claim 1, comprising:

said one or more integral connecting portions comprising one of tongue and groove type joints, lap type joints, one or more snap fit type joints, one or more finger type joints, locking type joints, click type joints, and dove tail type joint.

6. The custom manufactured cranial remodeling orthosis of claim 1, comprising: said one or more integral connecting portions integrally formed on each device portion of said at least three device portions; said one or more integral connecting portions used to couple and affix adjacent device portions of said at least three device portions together.

7. The custom manufactured cranial remodeling device of claim 1, comprising: said at least three device portions comprise a first device portion and a second device portion; said first device portion affixed to said second device portion utilizing said one or more integral connecting portions carried on a peripheral edge of said first device portion lockingly engaging corresponding connecting portions carried on said second device portion.

8. The custom manufactured cranial remodeling device of claim 1, comprising: said at least three device portions comprise a first device portion and a plurality of second device portions; said plurality of second device portions affixed to each other utilizing corresponding integral connecting portions of said plurality of integral connecting portions to form a second portion; and said first device portion affixed to said second device portion utilizing corresponding ones of said integral connecting portions.

9. A cranial remodeling orthosis device for modifying a shape of a particular subject's head, comprising: at least three device portions; each of said device portions of said at least three device portions comprising a continuous, monolithic outer surface over said outer surface entirety and a continuous, monolithic inner surface over said inner surface entirety; each of said device portions of said at least three device portions comprising one or more peripheral edges each disposed between said continuous, monolithic outer surface and said continuous monolithic inner surface; each of said device portions of said at least three device portions comprising a plurality of connecting portions disposed on one or more peripheral edges between said continuous, monolithic inner surface and said continuous, monolithic outer surface; and each of said connecting portions of said plurality of connecting portions configured to lockingly engage a corresponding connecting portion on an adjacent one or more of said device portions of said at least three device portions to form said cranial remodeling orthosis device having a continuous outer surface and a continuous inner surface.

10. The cranial remodeling orthosis of claim 9, comprising:

each of said integral connecting portions comprises one of portions of a tongue and groove type joint, portions of a lap type joint, portions of one or more snap fit joints, portions of one or more finger joints, portions of a locking type joint, portions of a click type joint, and portions of a dovetail type joint.

11. The cranial remodeling orthosis of claim 9, comprising:

each of said integral connecting portions comprising one of a projecting member projecting from said peripheral edge and a receiving member for receiving one said projecting member.

12. The cranial remodeling orthosis of claim 9, wherein: each device portion of said at least three device portions comprises additive manufacture material.

13. A custom manufactured cranial remodeling orthosis, comprising:

at least three portions; each portion of said at least three portions comprising additive manufacture material; each portion of said at least three portions comprising a continuous, monolithic outer surface and a continuous, monolithic inner surface, each portion of said at least three portions comprising a peripheral edge disposed between said continuous, monolithic outer surface, and said continuous, monolithic inner surface; and each portion of said at least three portions comprising one or both of a plurality of extending members extending from said each portion said peripheral edge and a plurality of receiving members formed in said each portion said peripheral edge; said plurality of extending members configured to lockingly affix together adjacent portions of said at least three portions to form a cranial remodeling orthosis having a smooth, continuous, monolithic external surface and a smooth, continuous, monolithic inner surface.

14. The custom manufactured cranial remodeling orthosis of claim 13, comprising: each said portion of said at least three portions comprises additive manufacture material.

* * * * *